United States Patent
Singh et al.

(10) Patent No.: US 9,242,021 B2
(45) Date of Patent: Jan. 26, 2016

(54) ADHESIVE COMPOSITION

(75) Inventors: Parminder Singh, San Francisco, CA (US); Gary W. Cleary, Los Altos Hills, CA (US); Valery G. Kulichikhin, Moscow (RU); Sergey Antonov, Moscow (RU)

(73) Assignees: Corium International, Inc., Menlo Park, CA (US); A.V. Topchiev Institute of Petrochemical Synthesis, Russian Academy of Sciences, Moscow (RU)

(*) Notice: Subject to any disclaimer, the term of this patent is extended or adjusted under 35 U.S.C. 154(b) by 2334 days.

(21) Appl. No.: 11/198,468

(22) Filed: Aug. 4, 2005

(65) Prior Publication Data

US 2006/0034905 A1    Feb. 16, 2006

Related U.S. Application Data

(60) Provisional application No. 60/599,593, filed on Aug. 5, 2004.

(51) Int. Cl.
| | |
|---|---|
| A61K 9/70 | (2006.01) |
| A61L 15/58 | (2006.01) |
| A61K 9/00 | (2006.01) |
| A61K 9/06 | (2006.01) |
| A61K 47/02 | (2006.01) |
| C09J 139/06 | (2006.01) |
| C09J 153/02 | (2006.01) |
| C09J 155/02 | (2006.01) |
| C08K 3/34 | (2006.01) |
| C08L 53/02 | (2006.01) |
| C08L 71/02 | (2006.01) |

(52) U.S. Cl.
CPC ............... *A61L 15/585* (2013.01); *A61K 9/006* (2013.01); *A61K 9/06* (2013.01); *A61K 9/7007* (2013.01); *A61K 9/7053* (2013.01); *A61K 47/02* (2013.01); *C09J 139/06* (2013.01); *C09J 153/02* (2013.01); *C09J 155/02* (2013.01); *C08K 3/346* (2013.01); *C08L 53/02* (2013.01); *C08L 71/02* (2013.01)

(58) Field of Classification Search
None
See application file for complete search history.

(56) References Cited

U.S. PATENT DOCUMENTS

| | | |
|---|---|---|
| 2,561,071 A | 7/1951 | Prisk |
| 2,579,403 A | 12/1951 | Slomowitz et al. |
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelson |
| 4,871,536 A | 10/1989 | Arraudeau et al. |
| 4,873,299 A | 10/1989 | Nawoakowsky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,973,468 A | 11/1990 | Chiang et al. |
| 4,983,395 A | 1/1991 | Chang et al. |

(Continued)

FOREIGN PATENT DOCUMENTS

| | | |
|---|---|---|
| CA | 2520986 | 4/2000 |
| CA | 2402021 | 9/2001 |

(Continued)

OTHER PUBLICATIONS

Southern Clay Products, "Cloisite 20A Typical Physical Properties Bulletin," 2 pages.*
U.S. Appl. No. 10/137,664, filed May 1, 2002, Cleary, et al.
U.S. Appl. No. 10/359,548, filed Feb. 5, 2003, Singh, et al.
U.S. Appl. No. 10/661,103, filed Sep. 12, 2003, Singh, et al.
U.S. Appl. No. 10/936,887, filed Sep. 8, 2004, Feldstein, et al.
U.S. Appl. No. 10/848,538, filed May 17, 2004, Singh, et al.
U.S. Appl. No. 11/028,703, filed Jan. 3, 2005, Feldstein, et al.
Aubin, et al., "Analysis of the glass transition temperature of miscible polymer blends", Macromolecules, vol. 21, pp. 2945-2949, (1988).
Bairamov, et al., "Kinetic parameters of poly(N-vinyl pyrrolidone) spontaneous mixing with short-chain poly(ethylene glycol)", Polym. Mater. Sci. Eng., vol. 82, pp. 7-8, (2000).

(Continued)

*Primary Examiner* — Brian Gulledge
(74) *Attorney, Agent, or Firm* — Judy M. Mohr; McDermott Will & Emery LLP

(57) ABSTRACT

An adhesive composition is described which has improved initial tack, long-term adhesion, water uptake and translucency characteristics and may be prepared by melt extrusion. Uses of these compositions are also described, for example, their use as blister pads and wound dressings.

31 Claims, No Drawings

(56) References Cited

U.S. PATENT DOCUMENTS

| | | | |
|---|---|---|---|
| 5,023,084 | A | 6/1991 | Chien et al. |
| 5,053,227 | A | 10/1991 | Chiang et al. |
| 5,057,500 | A | 10/1991 | Thornfeldt |
| 5,073,381 | A | 12/1991 | Ivan et al. |
| 5,102,662 | A | 4/1992 | Gallagher |
| 5,125,894 | A | 6/1992 | Phipps et al. |
| 5,133,970 | A | 7/1992 | Petereit et al. |
| 5,141,750 | A | 8/1992 | Lee et al. |
| 5,173,302 | A | 12/1992 | Holmblad et al. |
| 5,183,901 | A | 2/1993 | Login et al. |
| 5,196,405 | A | 3/1993 | Packman |
| 5,200,190 | A | 4/1993 | Azuma et al. |
| 5,206,385 | A | 4/1993 | Login et al. |
| 5,224,928 | A | 7/1993 | Sibalis et al. |
| 5,232,702 | A | 8/1993 | Pfister et al. |
| 5,234,690 | A | 8/1993 | Chiang et al. |
| 5,234,957 | A | 8/1993 | Mantelle |
| 5,240,995 | A | 8/1993 | Gyory et al. |
| 5,254,346 | A | 10/1993 | Tucker et al. |
| 5,270,358 | A | 12/1993 | Asmus |
| 5,276,079 | A | 1/1994 | Duan et al. |
| 5,296,512 | A | 3/1994 | Beier et al. |
| 5,300,291 | A | 4/1994 | Sablotsky et al. |
| 5,310,563 | A | 5/1994 | Curtis et al. |
| 5,322,689 | A | 6/1994 | Hughes et al. |
| 5,326,685 | A | 7/1994 | Gaglio et al. |
| 5,332,576 | A | 7/1994 | Mantelle |
| 5,338,490 | A | 8/1994 | Dietz et al. |
| 5,342,623 | A | 8/1994 | Enscore et al. |
| 5,344,394 | A | 9/1994 | Gyory et al. |
| 5,354,823 | A | 10/1994 | Tseng et al. |
| 5,362,420 | A | 11/1994 | Itoh et al. |
| 5,376,377 | A | 12/1994 | Gale et al. |
| 5,422,119 | A | 6/1995 | Casper |
| 5,438,076 | A | 8/1995 | Friedman et al. |
| 5,446,070 | A | 8/1995 | Mantelle |
| 5,456,745 | A | 10/1995 | Roreger et al. |
| 5,462,743 | A | 10/1995 | Turner et al. |
| 5,462,745 | A | 10/1995 | Enscore et al. |
| 5,492,943 | A | 2/1996 | Stempel |
| 5,508,024 | A | 4/1996 | Tranner |
| 5,508,367 | A | 4/1996 | Zajaczkowski |
| 5,527,271 | A | 6/1996 | Shah et al. |
| 5,543,148 | A | 8/1996 | Lapidus |
| 5,563,153 | A | 10/1996 | Mueller et al. |
| 5,575,654 | A | 11/1996 | Fontenot |
| 5,593,686 | A | 1/1997 | Kissel et al. |
| 5,594,068 | A | 1/1997 | Buchanan et al. |
| 5,599,373 | A * | 2/1997 | Zanuccoli ............ 71/21 |
| 5,614,178 | A | 3/1997 | Bloon et al. |
| 5,631,267 | A | 5/1997 | Gliech et al. |
| 5,633,010 | A | 5/1997 | Chen |
| 5,641,504 | A | 6/1997 | Lee et al. |
| 5,641,507 | A | 6/1997 | DeVillez |
| 5,643,187 | A | 7/1997 | Naestoft et al. |
| 5,645,062 | A | 7/1997 | Anderson et al. |
| 5,645,855 | A | 7/1997 | Lorenz |
| 5,656,286 | A | 8/1997 | Miranda et al. |
| 5,660,178 | A | 8/1997 | Kantner et al. |
| 5,662,925 | A | 9/1997 | Ebert et al. |
| 5,663,010 | A | 9/1997 | Stocchiero |
| 5,674,561 | A | 10/1997 | Dietz et al. |
| 5,700,478 | A | 12/1997 | Biegajski et al. |
| 5,702,721 | A * | 12/1997 | Horstmann et al. ........ 424/449 |
| 5,718,187 | A | 2/1998 | Pollock et al. |
| 5,718,886 | A | 2/1998 | Pellico |
| 5,719,197 | A | 2/1998 | Kanios et al. |
| 5,723,145 | A | 3/1998 | Shikinami et al. |
| 5,725,876 | A | 3/1998 | Mantelle et al. |
| 5,726,250 | A | 3/1998 | Zajaczkowski |
| 5,730,999 | A | 3/1998 | Lehmann et al. |
| 5,744,155 | A | 4/1998 | Freidman et al. |
| 5,762,956 | A | 6/1998 | Chien |
| 5,770,220 | A | 6/1998 | Meconi et al. |
| 5,773,490 | A | 6/1998 | Shikinami et al. |
| 5,780,050 | A | 7/1998 | Jain et al. |
| 5,785,527 | A | 7/1998 | Jensen et al. |
| 5,785,976 | A | 7/1998 | Westesen et al. |
| 5,788,983 | A | 8/1998 | Chien et al. |
| 5,800,832 | A | 9/1998 | Tapolsky et al. |
| 5,804,611 | A | 9/1998 | Takoh et al. |
| 5,827,525 | A | 10/1998 | Liao et al. |
| 5,830,932 | A | 11/1998 | Kay |
| 5,837,713 | A | 11/1998 | Gliech et al. |
| 5,846,558 | A | 12/1998 | Nielsen et al. |
| 5,851,549 | A | 12/1998 | Svec |
| 5,853,755 | A | 12/1998 | Foldvari |
| 5,858,332 | A | 1/1999 | Jensen et al. |
| 5,858,410 | A | 1/1999 | Muller et al. |
| 5,863,662 | A | 1/1999 | Hornby et al. |
| 5,876,746 | A | 3/1999 | Jona et al. |
| 5,879,691 | A | 3/1999 | Sagel et al. |
| 5,891,453 | A | 4/1999 | Sagel et al. |
| 5,900,249 | A | 5/1999 | Smith |
| 5,902,598 | A | 5/1999 | Chen et al. |
| 5,911,980 | A | 6/1999 | Samour et al. |
| 5,912,271 | A | 6/1999 | Brodine et al. |
| 5,916,587 | A | 6/1999 | Min et al. |
| 5,942,543 | A | 8/1999 | Ernst |
| 5,945,032 | A | 8/1999 | Breitenbach et al. |
| 5,945,457 | A | 8/1999 | Plate et al. |
| 5,948,416 | A | 9/1999 | Wagner et al. |
| 5,948,430 | A | 9/1999 | Zerbe et al. |
| 5,948,433 | A | 9/1999 | Burton et al. |
| 5,958,379 | A | 9/1999 | Regenold et al. |
| 5,958,446 | A | 9/1999 | Miranda et al. |
| 5,962,011 | A | 10/1999 | DeVillez |
| 5,972,377 | A | 10/1999 | Jona et al. |
| 5,976,565 | A | 11/1999 | Fotinos |
| 5,985,311 | A | 11/1999 | Cordes et al. |
| 5,985,860 | A | 11/1999 | Toppo |
| 5,985,990 | A | 11/1999 | Kantner et al. |
| 5,989,569 | A | 11/1999 | Dirksing et al. |
| 5,990,179 | A | 11/1999 | Gyori et al. |
| 5,993,836 | A | 11/1999 | Castillo |
| 5,993,849 | A | 11/1999 | Assmus et al. |
| 5,997,886 | A | 12/1999 | Peffly et al. |
| 6,004,566 | A | 12/1999 | Freidman et al. |
| 6,004,578 | A | 12/1999 | Lee et al. |
| 6,007,837 | A | 12/1999 | Enscore et al. |
| 6,024,976 | A | 2/2000 | Miranda et al. |
| 6,045,811 | A | 4/2000 | Dirksing et al. |
| 6,051,609 | A | 4/2000 | Miranda et al. |
| 6,063,399 | A | 5/2000 | Assmus et al. |
| 6,068,650 | A | 5/2000 | Hofmann et al. |
| 6,075,626 | A | 6/2000 | Mizutani et al. |
| 6,083,421 | A | 7/2000 | Huang et al. |
| 6,093,328 | A | 7/2000 | Santina |
| 6,096,328 | A | 8/2000 | Sagel et al. |
| 6,135,126 | A | 10/2000 | Joshi |
| 6,142,939 | A | 11/2000 | Eppstein et al. |
| 6,146,654 | A | 11/2000 | Kubo |
| 6,153,215 | A | 11/2000 | Samuelsen et al. |
| 6,162,456 | A | 12/2000 | Dunbar et al. |
| 6,165,499 | A | 12/2000 | Kleinsorgen et al. |
| 6,177,096 | B1 | 1/2001 | Zerbe et al. |
| 6,193,993 | B1 | 2/2001 | Musashi et al. |
| 6,197,331 | B1 | 3/2001 | Lerner et al. |
| 6,201,164 | B1 | 3/2001 | Wulff et al. |
| 6,212,671 | B1 | 4/2001 | Kanehira et al. |
| 6,221,341 | B1 | 4/2001 | Montgomery |
| 6,221,383 | B1 * | 4/2001 | Miranda et al. ............ 424/449 |
| 6,231,885 | B1 | 5/2001 | Carrarra |
| 6,248,363 | B1 | 6/2001 | Patel et al. |
| 6,264,981 | B1 | 7/2001 | Zhang et al. |
| 6,270,792 | B1 | 8/2001 | Guillemet et al. |
| 6,275,728 | B1 | 8/2001 | Venkatraman et al. |
| 6,306,370 | B1 | 10/2001 | Jensen et al. |
| 6,312,666 | B1 | 11/2001 | Oxman et al. |
| 6,312,670 | B1 | 11/2001 | Montgomery |
| 6,316,022 | B1 | 11/2001 | Mantelle et al. |
| 6,322,774 | B1 | 11/2001 | Jensen et al. |
| 6,329,472 | B1 | 12/2001 | Kim et al. |
| 6,368,576 | B1 | 4/2002 | Jensen et al. |

(56) References Cited

U.S. PATENT DOCUMENTS

| | | |
|---|---|---|
| 6,419,905 B1 | 7/2002 | Alvarez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,611,706 B2 | 8/2003 | Avrahami et al. |
| 6,638,528 B1 | 10/2003 | Kanios |
| 6,667,410 B2 | 12/2003 | Magnus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Cleary et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Kim et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,112,713 B2 | 9/2006 | Sceusa |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 2001/0006677 A1 | 7/2001 | Mcginity et al. |
| 2001/0021374 A1 | 9/2001 | Montgomery |
| 2001/0046471 A1 | 11/2001 | Marek et al. |
| 2002/0004190 A1 | 1/2002 | Diasti et al. |
| 2002/0009420 A1 | 1/2002 | McLaughlin |
| 2002/0048602 A1 | 4/2002 | Flore et al. |
| 2002/0076487 A1 | 6/2002 | Zajac |
| 2002/0106335 A1 | 8/2002 | Orlowski et al. |
| 2002/0131990 A1 | 9/2002 | Barkalow et al. |
| 2002/0197284 A1 | 12/2002 | Luo et al. |
| 2003/0055190 A1 | 3/2003 | Parker et al. |
| 2003/0100654 A1* | 5/2003 | Chheang et al. ............ 524/445 |
| 2003/0130427 A1* | 7/2003 | Cleary et al. ............... 525/192 |
| 2003/0152528 A1 | 8/2003 | Singh et al. |
| 2003/0152615 A1 | 8/2003 | Houze et al. |
| 2003/0170308 A1* | 9/2003 | Cleary et al. ............... 424/486 |
| 2003/0180229 A1 | 9/2003 | Kosti |
| 2003/0225356 A1* | 12/2003 | Kulichikhin et al. ........ 602/54 |
| 2003/0235549 A1 | 12/2003 | Singh et al. |
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0219111 A1 | 11/2004 | Kim et al. |
| 2004/0258723 A1 | 12/2004 | Singh et al. |
| 2005/0031554 A1 | 2/2005 | Kim et al. |
| 2005/0113510 A1 | 5/2005 | Feldstein et al. |
| 2005/0215727 A1 | 9/2005 | Feldstein et al. |
| 2006/0193793 A1 | 8/2006 | Kim et al. |
| 2006/0193794 A1 | 8/2006 | Kim et al. |

FOREIGN PATENT DOCUMENTS

| | | |
|---|---|---|
| CA | 2451431 | 1/2003 |
| CA | 2506073 | 6/2004 |
| DE | 8509793 | 5/1985 |
| DE | 4219368 | 6/1992 |
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |
| EP | 0737477 | 10/1996 |
| EP | 0838225 | 4/1998 |
| EP | 0848960 | 6/1998 |
| EP | 1066823 | 1/2001 |
| GB | 1108837 | 4/1968 |
| JP | 58-162681 | 9/1983 |
| JP | 59-196817 | 11/1984 |
| JP | 01-15152 A | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 10-017448 | 1/1998 |
| JP | 2001-213768 A | 7/2001 |
| JP | 2002-029949 | 1/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| RU | 1459215 | 11/1995 |
| RU | 1459215 A1 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 00/16725 | 3/2000 |
| WO | WO 00/69421 | 11/2000 |
| WO | WO 01/26637 | 4/2001 |
| WO | WO 01/68045 | 9/2001 |
| WO | WO 01/87276 | 11/2001 |
| WO | WO 02/04570 | 1/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/089046 | 10/2003 |
| WO | WO 03/099344 | 12/2003 |
| WO | WO 2004/045569 | 6/2004 |
| WO | WO 2004/054638 | 7/2004 |
| WO | WO 2004/071323 | 8/2004 |
| WO | WO 2004/093786 | 11/2004 |
| WO | WO 2004/103201 | 12/2004 |
| WO | WO 2005/027768 | 3/2005 |

OTHER PUBLICATIONS

Borodulina, et al. "Viscoelasticity of Pressure-sensitive adhesive and bioadhesive hydrogels under compressive load", Proceed. 24th Annual Meeting Adhesion Soc., pp. 147-149, (2001).

Chalykh, et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).

(56) References Cited

OTHER PUBLICATIONS

Chalykh, et al., "Fracture mechanics of poly(N-vinyl pyrrolidone)-poly(ethylene glycol) hydrogel adhesive joints," Polym. Mater. Sci. Eng., vol. 81, pp. 427-428, (1999).
Chalykh, et al., "Pressure-sensitive adhesion in the blends of poly(N-vinyl pyrrolidone) and poly(ethylene glycol) of disparate chain lengths," J. Adhesion, vol. 78, pp. 667-694, (2002).
Cleary, et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.
Database WPI Section Ch, Week 198451, Derwent Publications Ltd., London, GB; AN 1984-315114 & JP 59196817 A (Sekisuki Chem Ind Co Ltd) Nov. 8, 1984 abstract.
Database WPI Section Ch, Week 199150, Derwent Publications Ltd., London, GB; AN 1991-366353 & JP 03247334 A (Sumitomo Rubber Ind Ltd) Nov. 5, 1991 abstract.
Database WPI Section Ch, Week 199118, Derwent Publications Ltd., London, GB, AN 1991-128478 & JP 03066612 A (Sato Pharm Co Ltd) Mar. 22, 1991 abstract.
Database WPI Section Ch, Week 199627, Derwent Publications Ltd., London, GB; AN 1996-266746 & SU 1459215 A ( A Med Cardiology Res Centre) Nov. 20, 1995 abstract.
Emla Cream, (lidocaine 2.5% and prilocaine 2.5%), EMLA Anesthetic Disc, (lidocaine 2.5% and prilocaine 2.5% cream), Topical adhesive system, Detailed description.
Feldstein, et al., "A structure-property relationship and quantitative approach to the development of universal transdermal drug delivery system," NBC Risks, vol. 25, pp. 441-458, (1999).
Feldstein, et al., "Coherence of thermal transitions in poly(N-vinyl pyrrolidone)-poly(ethylene glycol) compatible blends: 1. Interrelations among the temperatures of melting, maximum cold crystallization rate and glass transition", Polymer, vol. 41, pp. 5327-5338, (2000).
Feldstein, et al., "Coherence of thermal transitions in poly(N-vinyl pyrrolidone)-poly(ethylene glycol) compatible blends: 2. The temperature of maximum cold crystallization rate versus glass transition", Polymer, vol. 41, pp. 5339-5348, (2000).
Feldstein, et al., "Coherence of thermal transitions in poly(N-vinyl pyrrolidone)-poly(ethylene glycol) compatible blends: 3. Impact of sorbed water upon phase behavior", Polymer, vol. 41, pp. 5349-5359, (2000).
Feldstein, et al., "Correlations between activation energy for debonding and that for self-diffusion in pressure-sensitive hydrogels", Proceed. 24th Annual Meeting Adhesion Soc., pp. 137-140, (2001).
Feldstein, et al., "Contribution of molecular mobility to debonding of pressure-sensitive adhesive hydrogels", Polym. Mater. Sci. Eng., vol. 81, pp. 467-468, (1999).
Feldstein, et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein, et al., "Effect of hydrophilic matrix hydration on transdermal drug delivery kinetics: II. In Vitro cytosine Delivery From Cypercuten TTS", Prediction of Percutaneous Penetration, vol. 4b, pp. 65-67, Brian, et al., (Eds.) (1996).
Feldstein, et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein, et al., "Effect of hydrophilic matrix hydration on transdermal drug delivery kinetics: IV. In Vitro-In Vivo correlation," Prediction of Percutaneous Penetration, vol. 4b, pp. 71-73, Brian, et al., (eds.) (1996).
Feldstein, et al., "Effects of chains orientation, free volume and interaction on glass transition in poly(N-vinyl pyrrolidone)-poly(ethylene glycol) blends involving a stoichiometric hydrogen-bonded network complex", Polym. Mater. Sci. Eng., vol. 82, pp. 365-366, (2000).
Feldstein, et al., "General approach to the molecular design of hydrophilic pressure-sensitive adhesives," Proc. 25th Ann. Mtg. And 2nd World Congress on Adhesion and Related Phenomena, Orlando, FL, vol. 1, pp. 292-294 (2002).
Feldstein, et al., "Molecular insight into rheologival and diffusion determinants of pressure sensitive adhesion", Proceed. 23rd Annual Meeting Adhesion Soc., pp. 54-56, (2000).
Feldstein, et al., "Peculiarities of glass transition temperature relation to the composition of poly(N-vinyl pyrolidone) blends with short chain poly(ethylene glycol)", Polymer, vol. 42, pp. 7719-7726, (2001).
Feldstein, et al., "Quantitative relationship between molecular structure and adhesion of PVP-PEG hydrogels", Polym. Mater. Sci Eng., vol. 81, pp. 465-466, (1999).
Feldstein, et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein, et al., "Universal hydrophilic drug-containing adhesive matrix for systemic and topical transdermal drug delivery", Proc. 1st World Meeting APGI/APV, Budapest, Sep. 2011, 2 pages, (1995).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.
International Search Report for PCT/US/2006/000098 Mailed Nov. 3, 2006.
International Search Report for PCT/US2006/0003091 Mailed Oct. 11, 2006.
International Search Report for PCT/US2006/018500 Mailed Sep. 21, 2006.
Kotomin, et al., "Squeeze-recoil analysis of adhesive hydrogels and elastomers", Polym. Mater. Sci. Eng., vol. 81, pp. 425-426, (1999).
Kotomin, et al., "Durability and fracture of some visceolastic adhesives," Proceed. of the 23rd Annual Meeting of the Adhesion Soc., pp. 413-415, (2000).
MSDS (Material Safety Data Sheet), Lactic Acid, No. L0522, (2008).
Patent Abstracts of Japan, vol. 017, No. 055 (C-I023) Feb. 3, 1993 & JP 04 266818 A (Sekisui Chem Co Ltd), Sep. 22, 1992 abstract.

(56) References Cited

OTHER PUBLICATIONS

Roos, et al., "Probe tack investigation of poly(vinyl pyrrolidone)-poly(ethylene glycol) blends", Proceed. 24th Annual Meeting Adhesion Soc., pp. 277-279, (2001).

Sintov, et al., "Radiofrequency-driven skin microchanneling as a new way for electrically assisted transdermal delivery of hydrophilic drugs", J. Contr.Release, vol. 89, pp. 311-320, (2003).

Supplementary European Search Report for EP04783729.9 Mailed Jun. 5, 2009.

Vartapian, et al., "Self-diffusion in poly(N-vinyl pyrrolidone)-poly(ethylene glycol) systems", Colloid Polym. Sci., vol. 279, pp. 532-538, (2001).

Vartapian, et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).

U.S. Appl. No. 11/150,811, filed Jun. 10, 2005, Feldstein, et al.

* cited by examiner

ADHESIVE COMPOSITION

CROSS-REFERENCE TO RELATED APPLICATIONS

This application claims priority under U.S.C. §119(e)(1) to Provisional U.S. Patent Application Ser. No. 60/599,593, filed Aug. 5, 2004. The disclosure of the aforementioned application is incorporated by reference in its entirety.

FIELD OF THE INVENTION

This invention relates generally to skin-contacting adhesive compositions, and more particularly relates to a novel composition useful in a variety of contexts including as a blister patch, or the like that is applied to an individual's skin or other body surface.

BACKGROUND OF THE INVENTION

Various types of bandages and wound dressings are known and used to protect wounds, burns and blisters. Typically, wound dressings are fabricated with an absorbent material so that wound exudate is removed and the wound dries, facilitating healing. Wound dressings may also contain one or more pharmacologically active agents such as antibiotics, local anesthetics, or the like. Commonly used wound dressings include fibrous materials such as gauze and cotton pads, which are advantageous in that they are absorbent but problematic in that fibers may adhere to the wound or newly forming tissue, causing wound injury upon removal. Other wound dressings have been prepared with foams and sponges, but the absorbance of these materials is often limited. Furthermore, such wound dressings require the use of adhesive tape, as they are not themselves adhesive. Finally, many of these wound dressings are not translucent or transparent, thus rendering it difficult to monitor healing without removal of the dressing.

To improve the absorbance of conventional fibrous wound dressings, water-swellable polymers or "hydrogels" have been incorporated into gauze or other fibrous materials for application to a wound. For example, U.S. Pat. No. 5,527,271 to Shah, et al. describes a composite material made from a fibrous material, such as cotton gauze, impregnated with a thermoplastic hydrogel-forming copolymer containing both hydrophilic and hydrophobic segments. While the wound dressings are described as having increased absorptive capacity, the adhesion of fibers to the wound or newly forming tissue remains a significant disadvantage.

Another approach has been to use water-swellable polymeric materials instead of gauze, cotton, and the like. Wound-contacting surfaces made of such materials are not only more absorbent than conventional fibrous materials, they are also advantageous in that there is no risk of fiber adhesion during wound healing and upon removal of the wound dressing. Such wound dressings are disclosed, for example, in U.S. Pat. No. 4,867,748 to Samuelsen, which describes the use of an absorbent wound-contacting composition made from a water-soluble or water-swellable hydrocolloid blended with or dispersed in a water-insoluble, viscous, elastomeric binder. U.S. Pat. No. 4,231,369 to Sorensen et al. describes "hydrocolloid plasters" as sealing materials for ostomy devices, the materials consisting of a continuous hydrophobic phase made from a hydrophobic pressure-sensitive adhesive, an elastomeric plasticizer, and a tackifying resin, with a discontinuous phase dispersed therein consisting of a water-soluble or water-swellable polymer. Such plasters are also described in U.S. Pat. No. 5,643,187 to Naestoft et al. U.S. Pat. No. 6,201,164 to Wulff et al. describes a somewhat different type of hydrocolloid wound gel, consisting of a water-insoluble, water-swellable, crosslinked cellulose derivative, an alginate, and water.

Hydrogel bandages have also been employed in wound dressings, as described, for example, in U.S. Pat. No. 4,093,673 to Chang et al. Hydrogel bandages are made from a liquid absorbing crosslinked polymer and have a high water content prior to use. The high water content causes the hydrogel to exhibit very little or no adhesion, requiring the use of adhesive tape or a plaster such as $2^{nd}$ Skin® dressing available from Spenco Medical Ltd., U.K.

However, in spite of the advances in the art, numerous problems continue to be encountered with gel-based wound dressings made with hydrocolloids and hydrogels. The reason for this is, in part, that there are conflicting requirements for an ideal material. The material should not be so adhesive that it tends to adhere to a wound and thus cause pain or further injury upon removal. However a wound dressing should adhere sufficiently to a body surface so that separate adhesive tapes and adhesive plasters are not necessary. Peripheral adhesives can be used, but require an additional manufacturing step. In addition, a wound dressing should conform to the contours of the skin or other body surface, both during motion and at rest. For wound dressings that also serve as a cushioning pad, higher cohesive strength materials should be used, without any loss in adhesion.

Many of these problems are addressed by the adhesive compositions described in U.S. patent application Publication No. 2003/0170308 to Cleary et al. and U.S. patent application Publication No. 2003/0225356 to Kulichikhin et al. However, in spite of these advances in the art, there remains a need for self adhering dressings which provide instant tack and prolonged skin adhesion, greater fluid handling capability, higher cohesive strength, decreased cold flow, less erosion, controlled active delivery, ease of manufacturability, and translucency. The present invention addresses those needs, and provides for formulations having increased resistance to cold flow and better tackiness to dry skin, as compared to the formulations described in U.S. patent application Publication No. 2003/0170308. The formulations described in U.S. patent application Publication No. 2003/0225356 also have such properties, but the instant formulations provide for higher moisture uptake without the loss of adhesion.

SUMMARY OF THE INVENTION

One aspect of the invention relates to an adhesive composition comprising: a hydrophobic polymer; an elastomeric plasticizer; a tackifying resin; a hydrophilic polymer; a complementary polymer capable of hydrogen bonding to the hydrophilic polymer; and clay particles.

Another aspect of the invention pertains to an adhesive composition comprising: a hydrophobic polymer selected from polyisoprenes, butyl rubbers styrene-isoprene-styrene block copolymers, and styrene-butadiene-styrene block copolymers; an elastomeric plasticizer selected from styrene-based plasticizers, low molecular weight polyisobutylenes, low molecular weight polyisoprene rubbers, and combinations thereof; a tackifying resin selected from hydrogenated hydrocarbon resins, hydrocarbon resins and synthetic polyterpene resins; a hydrophilic polymer is selected from poly(N-vinyl lactams), poly(N-vinyl amides), poly(N-vinyl acrylamides), poly(N-alkylacrylamides), polyacrylic acids, polymethacrylic acids, polyvinyl alcohol, polyvinylamine, cellulose derivatives, polysaccharides, and copolymers and blends thereof; a complementary polymer selected from low molecular weight polyalkylene glycols, low molecular weight polyalcohols, monomeric and oligomeric alkylene glycols, ether alcohols, carbonic diacids, and alkane diols; and phyllosilicate particles.

Still another aspect of the invention pertains to an adhesive cushion for application to the skin, comprising a skin-contacting layer of the adhesive composition of the invention, and a backing layer.

Yet another aspect of the invention relates to a wound dressing comprising a laminated composite of a body facing layer having a body-contacting surface, and an outwardly facing non-occlusive backing layer, wherein at least a portion of the body-contacting surface is comprised of the adhesive composition of the invention.

Another aspect of the invention relates to a transdermal drug delivery device comprised of a drug reservoir containing a therapeutically effective amount of an active agent, an outwardly facing backing layer, and a means for affixing the device to a body surface comprising the adhesive composition of the invention.

Still another aspect of the invention relates to a slowly dissolving film comprising: a hydrophilic polymer selected from poly(N-vinyl lactams), poly(N-vinyl amides), poly(N-vinyl acrylamides), poly(N-alkylacrylamides), polyacrylic acids, polymethacrylic acids, polyvinyl alcohol, polyvinylamine, cellulose derivatives, polysaccharides, and copolymers and blends thereof; a complementary polymer selected from low molecular weight polyalkylene glycols, low molecular weight polyalcohols, monomeric and oligomeric alkylene glycols, ether alcohols, carbonic diacids, and alkane diols; and clay particles.

Another aspect of the invention relates to a slowly dissolving film comprising: a hydrophilic polymer selected from poly(N-vinyl lactams), poly(N-vinyl amides), poly(N-vinyl acrylamides), poly(N-alkylacrylamides), polyacrylic acids, polymethacrylic acids, polyvinyl alcohol, polyvinylamine, cellulose derivatives, polysaccharides, and copolymers and blends thereof; a complementary polymer selected from low molecular weight polyalkylene glycols, low molecular weight polyalcohols, monomeric and oligomeric alkylene glycols, ether alcohols, carbonic diacids, and alkane diols; a water-swellable water-insoluble polymer; and clay particles.

DETAILED DESCRIPTION OF THE INVENTION

The present invention is an adhesive composition that finds utility in numerous applications as detailed in part V below. In particular, due to the skin-contacting adhesive properties under moist and load-bearing conditions, it finds particular utility for medical films used to treat blisters and in foot care. For example, the adhesive can be applied to the sole of the foot, to the toes or to any other location on the foot to treat pain caused by a callus, corn, bunion, or blister, by providing a cushion effect.

The adhesive composition is comprised of: a hydrophobic polymer; an elastomeric plasticizer; a tackifying resin; a hydrophilic polymer; a complementary polymer capable of hydrogen bonding to the hydrophilic polymer; and clay particles.

The composition of the invention provides for prolonged hydrations such that it is able to absorb water found in the environment or from the body surface to which it is applied. In particular, it is preferred that the adhesive remain translucent upon water uptake over a typical wearing time of 72 hours. The composition has rapid initial tack in that it grabs quickly to the skin surface during application, is pressure and body sensitive and able to maintain excellent adhesion while subjected to load bearing forces, such as those experienced when the adhesive is positioned on a lower foot surface. In this case the appropriate compromise between adhesion and elastic recovery should be found: to preserve adhesion without prominent cold flow. In addition, the composition is preferably skin and user friendly for at least 72 hours of continuous wear.

The aforementioned characteristics are readily achieved by careful selection of the individual components in the adhesive composition, as well as adjusting one or more parameters during fabrication.

Before describing the detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive and it is further to be understood that unless otherwise indicated this invention is not limited to specific materials, active agents, additives, and so forth, as such may vary. For example, when an example is said to "include" a specific feature, that is intended to imply that it may have that feature but not that such examples are limited to those that include that feature. Thus, for example, reference to "a hydrophobic polymer" includes a mixture of two or more such polymers, and so forth. Finally, it must be noted that, as used in this specification and the appended claims, the singular forms "a," "an" and "the" include plural referents unless the context clearly dictates otherwise. Thus, for example, reference to "an active agent" includes a mixture of two or more such agents, and the like.

I. Definitions

In describing and claiming the present invention, the following terminology will be used in accordance with the definitions set out below.

The terms "hydrophobic polymer" and "hydrophilic polymer" are intended to be defined relative to the amount of water vapor absorbed by polymers at 100% relative humidity. According to this classification, hydrophobic polymers absorb only up to 1 wt % of water at 100% relative humidity (rh), while moderately hydrophilic polymers absorb 1-10 wt % of water, hydrophilic polymers are capable of absorbing more than 10 wt % of water, and hygroscopic polymers absorb more than 20 wt % of water.

The terms "tack" and "tacky" are qualitative. However, the terms "substantially nontacky," "slightly tacky" and "tacky," as used herein, may be quantified using the values obtained by a PSA Tack Determination/Polyken Probe method (Solutia, Inc.). By "substantially nontacky" is meant an adhesive that has a tack value that is less than about 25 g-cm/sec, by "slightly tacky" is meant an adhesive that has a tack value in the range of about 25 g-cm/sec to about 100 g-cm/sec, and by "tack" is meant an adhesive that has a tack value of at least 100 g-cm/sec.

The term "translucent" is used to signify a material capable of transmitting light so that objects or images can be seen through the material. Translucent materials herein may or may not be "transparent," meaning that the material is optically clear. The term "translucent" indicates that a material is not "opaque," in which case objects and images cannot be seen through the material.

The term "active agent" refers to a chemical material or compound suitable for topical or transdermal administration and that induces a desired effect. The terms include agents that are therapeutically effective, prophylactically effective, and cosmetically effective agents. Also included are pharmaceutically acceptable, pharmacologically active derivatives of those active agents specifically mentioned herein, including, but not limited to, salts, esters, amides, prodrugs, active metabolites, inclusion complexes, analogs, and the like, which also induce the desired effect. The terms "active agent", "drug" and "therapeutic agent" are used interchangeably herein.

By "transdermal" delivery is meant administration of an active agent to a body surface of an individual so that the agent passes through the body surface, e.g., skin, and into the individual's blood stream. The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

The term "body surface" is used to refer to skin or mucosal tissue, including the interior surface of body cavities that have a mucosal lining. The term "skin" should be interpreted as including "mucosal tissue" and vice versa.

The term "therapeutically effective amount" is intended to mean the amount of an active agent that is nontoxic but sufficient to provide the desired effect. The amount that is "effective" will vary from subject to subject, depending on the age and general condition of the individual, the particular active agent or agents, and the like. Thus, it is not always possible to specify an exact effective amount. However, an appropriate effective amount in any individual case may be determined by one of ordinary skill in the art using routine experimentation. Furthermore, the exact effective amount of an active agent incorporated into the adhesive of the invention is not critical, so long as the concentration is within a range sufficient to permit ready application of the formulation so as to deliver an amount of the active agent that is within a therapeutically effective range.

II. Compositions

The desirable adhesive characteristics are achieved by selection of the individual components as well as adjusting one or more parameters during fabrication. For example, the adhesive strength of the adhesive can be controlled during manufacture in order to increase, decrease, or eliminate adhesion. This can be accomplished by varying the type and/or amount of different adhesive components, or by changing the mode of fabrication. For example, incorporating greater amounts of the elastomeric plasticizer and the tackifying resin will increase tack, while reducing the amounts of those components or incorporating detackifier additives or increasing the level of powdered hydrophilic components, will decrease tack. Also, with respect to the fabrication process, adhesives prepared using a conventional melt extrusion process tend to be more tacky, while adhesives prepared by a molding procedure tend to have lower tack. In addition, adhesives may be rendered translucent by changing the relative quantities of certain components (e.g., by decreasing the amount of clay), or by changing the conditions (temperature, extrusion rate, thickness, etc.) of the fabrication method.

For multicomponent systems such as the compositions described herein, problems associated with compatibility or phase diagrams play an important role. By modifying the temperature of a composition, it is possible to attain a definite level of miscibility (transparency) which can be "frozen" at cooling and solidification of the formulation as whole. In this manner, at extrusion the phase equilibrium can be changed and the low molecular weight tacky components can migrate to the periphery of the manufactured film due to the action of complex shear and extension fields.

Furthermore, the degree to which the adhesive will swell upon contact with water can be varied by selecting different water-swellable and water-soluble hydrophilic polymers and their ratio. Combination of water-swellable and water-soluble hydrophilic polymers allows us to control the swelling degree of the composition and to create a capability of the composition to be re-applied to the body surface after an additional wetting.

In one embodiment, the composition of the invention is comprised of a hydrophobic polymer; an elastomeric plasticizer; a tackifying resin; a hydrophilic polymer; a complementary polymer capable of hydrogen bonding to the hydrophilic polymer; and clay particles. It is understood that the composition may include a combination of more than one hydrophobic polymer, a combination of more than one elastomeric plasticizer, a combination of more than one tackifying resin, a combination of more than one hydrophilic polymer, a combination of more than one complementary polymer, and/or a combination of more than one type of clay particles.

Typically, the composition will be about 1-40 wt % hydrophobic polymer; about 1-30 wt % elastomeric plasticizer; about 1-30 wt % tackifying resin; about 1-50 wt % hydrophilic polymer; about 1-30 wt % complementary polymer; and about 1-30 wt % clay particles.

One preferred embodiment has 15-25 wt % hydrophobic polymer; about 10-20 wt % elastomeric plasticizer; about 13-20 wt % tackifying resin; about 20-30 wt % hydrophilic polymer; about 8-18 wt % complementary polymer; and about 8-15 wt % clay particles.

Yet another preferred embodiment has 19-21 wt % hydrophobic polymer; about 14-16 wt % elastomeric plasticizer; about 16-18 wt % tackifying resin; about 23-25 wt % hydrophilic polymer; about 11-13 wt % complementary polymer; and about 11-13 wt % clay particles.

For some applications, for example as a slowly dissolving film, the hydrophobic polymer and elastomeric plasticizer can be omitted. Such formulations would typically comprise about 50-65 wt % hydrophilic polymer; about 35-45 wt % complementary polymer; and about 1-5 wt % clay particles.

These percentages are intended to merely be illustrative of the compositions of the invention. There are other factors that can be taken into consideration when ascertaining the actual materials and quantities to be used in the formulations. For example, the weight ratios of certain materials can be selected so as to optimize the adhesive strength, cohesive strength and water sorption of the composition. Similarly, the weight ratios of these same materials can be selected so as to render the composition translucent, which is a desirable characteristic for some applications of the adhesive.

In an exemplary embodiment of the invention, the composition comprises: a hydrophobic polymer selected from polyisoprenes, butyl rubbers, styrene-isoprene-styrene block copolymers, and styrene-butadiene-styrene block copolymers; an elastomeric plasticizer selected from styrene-based plasticizers, low molecular weight polyisobutylenes, low molecular weight polyisoprene rubbers, and combinations thereof, a non-polar tackifying resin selected from hydrogenated hydrocarbon resins, hydrocarbon resins and synthetic polyterpene resins; a hydrophilic polymer selected from poly (N-vinyl lactams), poly(N-vinyl amides), poly(N-vinyl acrylamides), poly(N-alkylacrylamides), polyacrylic acids, polymethacrylic acids, polyvinyl alcohol, polyvinylamine, and copolymers and blends thereof; a complementary polymer selected from low molecular weight polyalkylene glycols, low molecular weight polyalcohols, monomeric and oligomeric alkylene glycols, ether alcohols, carbonic diacids, and alkane diols; and phyllosilicate particles.

A. Hydrophobic Polymer

Suitable hydrophobic polymers include, by way of illustration and not limitation, polyisobutylenes, butyl rubbers, natural rubber adhesives, vinyl ether polymers, polysiloxanes, polyisoprenes, styrene-isoprene-styrene block copolymers, styrene-butadiene-styrene block copolymers, isobutylene-isoprene copolymers, butadiene acrylonitrile rubber, polychloroprenes, ethylene-propylene-diene terpolymers, acrylates, and combinations thereof. Polyisoprenes, butyl rubbers, styrene-isoprene-styrene block copolymers, and styrene-butadiene-styrene block copolymers are particularly well suited for use in the invention.

In one embodiment of the invention, the hydrophobic polymer is a triblock styrenic copolymer such as styrene-isoprene-styrene (SIS) or styrene-butadiene-styrene (SBS) and can further comprises the diblock copolymer, styrene-isoprene (SI) block copolymer.

Commercially available styrene-based block copolymers such as the Vector series (available from Dexco Polymers) are particularly useful in the invention. These include the SIS Vector 4111 (18 wt % styrene/82 wt % isoprene) and 4411 (44 wt % styrene/56 wt % isoprene) as well as SIS/SI mixtures such as Vector 4113 (18 wt % SI diblock; overall 15 wt % styrene/85 wt % isoprene), Vector 4114 (42 wt % SI diblock; overall 15 wt % styrene/85 wt % isoprene), Vector 4213 (25 wt % SI diblock; overall 25 wt % styrene/75 wt % isoprene) and Vector 4215 (18 wt % SI diblock; overall 30 wt % styrene/70 wt % isoprene).

In another embodiment of the invention, the hydrophobic polymer is a polyisoprene or a butyl rubber. Commercially available polyisoprenes such as the high molecular weight polyisoprene rubber Natsyn® 2210 (Goodyear Tire and Rubber), and butyl rubbers such as the high molecular weight butyl rubber BR 065 (Exxon), are particularly useful in the invention.

In the case of unsaturated rubbers a curing agent may be added to fix the structure of the composition, as well as to prevent cold flow. Since it is desirable to reach specific rheological properties, namely diminished cold flow, i.e., substantially total elastic recovery, unsaturated hydrophobic components (butyl rubber, natural rubber, synthetic polyisoprene rubber, etc.) are preferably crosslinked. Polymers containing double bonds undergo a process of chemical crosslinking with formation of covalent bonds. The density of the resultant chemical network should not be too high, in order to preserve the desired tack. The number of crosslinks in the volume unit can be controlled by the nature and amount of crosslinkers, as well as by the temperature-time procedure followed. Phenolformaldehyde resins and alkylphenolformaldehyde resins are suitable crosslinkers for butyl rubber, while dicumyl peroxide can be used for polyisoprenes.

The most convenient method of monitoring the degree of crosslinking involves measurement of the change in melt viscosity over time. The resulting rheokinetic curve demonstrates the rate of crosslinking and the plateau region corresponds to the completion of the chemical interaction of double bonds of unsaturated hydrophobic polymers with the crosslinkers.

In the case of triblock-copolymers, e.g. SIS or SBS, their solidification occurs as they cool due to the segregation of styrene blocks and their transition to a glassy state. At ambient temperature the elastic recoil of triblock-copolymer formulations exceeds 90%. The presence of elastomeric isoprene or butadiene blocks in the macromolecules of SIS and SBS, as well as the additional components of the hydrophobic phase (e.g., plasticizers), results in the desired tack and adhesive properties.

B. Elastomeric Plasticizer

The elastomeric plasticizer is preferably selected so as to be compatible with triblock-copolymers, i.e., forms a solution with multiblock-copolymers inside the definite temperature-concentration region of the phase diagram. Thus, one of skill in the art can readily use phase diagrams of the hydrophobic phase components for guidance concerning the appropriate amounts of each component to use.

Suitable elastomeric plasticizers include block polymers having a "multiarmed $(AB)_x$," configuration, where for example, A is a polymerized block comprising aryl-substituted vinyl monomers, preferably styrene, α-methyl styrene, vinyl toluene, and the like, B is an elastomeric, conjugated polybutadiene or polyisoprene block, and x has a value of 3 or more. Preferred plasticizers are styrene-based polymers, particularly styrene-butadiene block copolymers and styrene-isoprene block copolymers, and combinations thereof. Many of these are readily available commercially, such as the styrene-isoprene block copolymer sold under the name LVSI 101 (Kraton).

The elastomeric plasticizer can also be a low molecular weight polyisobutylene, or a low molecular weight polyisoprene rubber (MW=20,000-100,000) such as cis-1,4 polyisoprene (e.g., Isolene® 400 from Elementis Specialties Performance Polymers), optionally mixed with paraffin oil.

In one embodiment of the invention, the hydrophobic phase-elastomeric plasticizer includes both a block polymer (e.g., styrene) and a low molecular weight polyisoprene rubber (e.g. cis-1,4 polyisoprene).

C. Tackifying Resin

The tackifying resin is a relatively low molecular weight resin (weight average molecular weight generally less than about 50,000) having a fairly high glass transition temperature. Its function is to increase the strength of adhesion bonds. Tackifying resins include, for example, rosin derivatives, terpene resins, and synthetic or naturally derived petroleum resins. Preferred tackifying resins herein are generally nonpolar tackifying resins selected from the group consisting of hydrogenated hydrocarbon resins, hydrocarbon resins and synthetic polyterpene resins. The tackifying resin is preferably miscible with hydrophobic polymer/plasticizer composition to provide a ternary solution. Commercially available resins within these classes include Regalrez® 1085 (hydrogenated hydrocarbon resin) and Regalite Resins such as Regalite® 9100 (partially hydrogenated hydrocarbon resin, available from Hercules); Escorez® 1304 and Escorez® 1102 (hydrocarbon resins), and Escorez® 5380 (cyclicaliphatic hydrocarbon resin) available from Exxon Chemical Company, Wingtack® 95 and Wingtack® 85 (synthetic polyterpene resins), available from Goodyear Tire and Rubber.

D. Hydrophilic Polymer

Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly(N-vinyl lactams), poly(N-vinyl amides), poly(N-vinyl acrylamides), poly(N-alkylacrylamides), substituted and unsubstituted acrylic and methacrylic acid polymers (e.g., polyacrylic acids and polymethacrylic acids), polyvinyl alcohol (PVA), polyvinylamine, copolymers and blends thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Non-limiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly(N-vinyl amides) include, by way of example, N-vinyl acetamide.

Poly(N-alkylacrylamides) include, by way of example, poly(methacrylamide) and poly(N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Cellulose derivatives, mainly water-soluble hydroxypropylcellulose (HPC) of different molecular weight are also suitable for use as hydrophilic polymers. Upon melting, cellulose derivatives form a liquid crystalline (LC) melt having a cholesteric structure. That is to say, stiff macromolecules are positioned, not in a chaotic way as in isotropic polymers, but rather to form a layered structure; the long axes of macromolecules are oriented inside the layer in one direction, and this direction changes by a slight angle when passing from one layer to other, forming a so-called cholesteric macrohelix. The existence of interplanar spaces, and the formation of long fibers during processing of these polymers provides numerous advantages. At cooling, the LC melt of HPC is a solid polymer with complex phase structure.

Polysaccharides such as water-swellable agar are also suitable for use as hydrophilic polymers, and allow for the storage of a significant amount of moisture.

Preferred hydrophilic polymers herein are the following: poly(N-vinyl lactams), particularly polyvinyl pyrrolidone (PVP) and polyvinyl caprolactam (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 50,000 to 2,000,000, more typically in the range of approximately 100,000 to 1,500,000, also in some cases in the range of approximately 500,000 to 1,500,000.

E. Complementary Polymer

The complementary polymer is capable of hydrogen bonding to the hydrophilic polymer, and optionally is capable of ionically or covalently bonding to the hydrophilic polymer as well. The complementary polymer can be a polymer, and oligomer, or any low molecular weight substance that is capable of forming hydrogen bonds with the hydrophilic polymer.

Preferably, the complementary polymer is a complementary oligomer. Preferred complementary oligomers are terminated with hydroxyl groups, amino or carboxyl groups. The oligomer typically has a glass transition temperature $T_g$ in the range of about −100° C. to about −30° C. and a melting temperature $T_m$ lower than about 20° C. The oligomer may be also amorphous. The difference between the $T_g$ values of the hydrophilic polymer and the oligomer is preferably greater than about 50° C., more preferably greater than about 100° C., and most preferably in the range of about 150° C. to about 300° C. The hydrophilic polymer and complementary oligomer should be compatible, i.e. capable of forming a homogeneous blend that exhibits a single $T_g$, intermediate between those of the unblended components.

Generally, the complementary oligomer will have a molecular weight in the range from about 45 to about 800, preferably in the range of about 45 to about 600. The complementary oligomer is preferably a low molecular weight polyalkylene glycol (molecular weight 300-600) such as polyethylene glycol 400, which can also serve as a low molecular weight plasticizer, and can be carboxyl-terminated or amino-terminated. Alternatively, a different compound can be incorporated as an additional low molecular weight plasticizer, in which case any of the low molecular weight plasticizers described below can be used. In one embodiment of the invention, the complementary oligomer is a complementary low molecular weight or oligomeric plasticizer that contains at least two functional groups per molecule that are capable of hydrogen bonding to the hydrophilic polymer.

Other examples of suitable complementary oligomers include, but are not limited to, low molecular weight polyalcohols (e.g. glycerol), monomeric and oligoalkylene glycols such as ethylene glycol and propylene glycol, ether alcohols (e.g., glycol ethers), carbonic diacids, alkane diols from butane diol to octane diol, including carboxyl-terminated and amino-terminated derivatives of polyalkylene glycols noted above. Polyalkylene glycols, optionally carboxyl-terminated, are preferred herein, and polyethylene glycols having a molecular weight in the range of about 300 to 600 are optimal complementary oligomers.

It will be appreciated from the foregoing that a single compound, e.g., a low molecular weight polyalkylene glycol such as polyethylene glycol having a molecular weight in the range of about 300 to 600, can serve as both the complementary oligomer and the elastomeric plasticizer.

As the complementary oligomer may itself act as a plasticizer, it is not generally necessary to incorporate an added plasticizer. However, inclusion of an additional low molecular weight plasticizer in the composition is optional and may, in some cases, be advantageous. Suitable low molecular weight plasticizers include: dialkyl phthalates, dicycloalkyl phthalates, diaryl phthalates, and mixed alkyl-aryl phthalates, as represented by dimethyl phthalate, diethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trimethyl citrate, triethyl citrate, tributyl citrate, acetyl triethyl citrate, and trihexyl citrate; dialkyl adipates such as dioctyl adipate (DOA); also referred to as bis(2-ethylhexyl)adipate), diethyl adipate, di(2-methylethyl)adipate, and dihexyl adipate; dialkyl tartrates such as diethyl tartrate and dibutyl tartrate; dialkyl sebacates such as diethyl sebacate, dipropyl sebacate and dinonyl sebacate; dialkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and mixtures thereof. Preferred plasticizers are triethyl citrate, diethyl phthalate, and dioctyl adipate, with dioctyl adipate most preferred.

F. Clay Particles

The clay particles used in the composition of the invention are responsible for many of the beneficial aspects of the invention. For example, the clay particles: help to provide a wicking action to remove moisture from the skin surface and store it; reinforce the yield behavior that prevents the cold flow; help the composition maintain its adhesive nature as well as providing structural support to supply the high elastic recoil at application of the composition on the sole of foot, introduce nanospaces that can function to trap active ingredients and then release them upon certain conditions, e.g., upon contact with wound exudate, and so forth.

In general, clays have a layered structure and the space between neighbor platelets, for example in Na-montmorillonite, is around 1 nm. In the bulk state, clay materials are typically plastic when moist but hard when dried, and are often composed mainly of fine platelets of hydrous aluminum silicates, alone or in combination with other minerals. The individual clay platelets are flexible and transparent. Due to the presence on the surface of many functional groups, clays are able to interact with other components of the formulation. Negative charges on the particles are compensated by counterions, for example Na+, Ca++, Ag+, and so forth, or a combination thereof. Therefore, ion interaction between the charged clay platelets and other components is possible. In particular, suitable clay particle materials are selected from the group consisting of phyllosilicates (layered silicates) and layered double hydroxides (minerals and synthetic materials with positively charged brucite-type layers of mixed metal hydroxides). Such materials are described in detail in references such as "Polymer-Clay Nanocomposites", ed. T. J. Pinnavaia and G. W. Beall (Wiley Series in Polymer Science, John Wiley & Sons, Ltd., ©2000), the disclosure of which is incorporated herein by reference.

In one embodiment of the invention, the phyllosilicate is selected from the group consisting of allophane (hydrated aluminum silicate); apophyllite (hydrated potassium sodium calcium silicate hydroxide fluoride); bannisterite (hydrated potassium calcium manganese iron zinc aluminum silicate hydroxide); carletonite (hydrated potassium sodium calcium silicate carbonate hydroxide fluoride); cavansite (hydrated calcium vanadate silicate); chrysocolla (hydrated copper aluminum hydrogen silicate hydroxide); clay minerals (described in detail below); delhayelite (hydrated sodium potassium calcium aluminum silicate chloride fluoride sulfate); elpidite (hydrated sodium zirconium silicate); fedorite (hydrated potassium sodium calcium silicate hydroxide fluoride); franklinfurnaceite (calcium iron aluminum manganese zinc silicate hydroxide); franklinphilite (hydrated potassium manganese aluminum silicate); gonyerite (manganese magnesium iron silicate hydroxide); gyrolite (hydrated calcium silicate hydroxide); kanemite; kenyaite; leucosphenite (hydrated barium sodium titanium boro-silicate); magadiite; makatite; micas such as biotite (potassium iron magnesium aluminum silicate hydroxide fluoride), lepidolite (potassium lithium aluminum silicate hydroxide fluoride), muscovite (potassium aluminum silicate hydroxide fluoride), paragonite (sodium aluminum silicate hydroxide), phlogopite (potassium magnesium aluminum silicate hydroxide fluoride) and zinnwaldite (potassium lithium aluminum silicate hydroxide fluoride); minehillite (hydrated potassium sodium calcium zinc aluminum silicate hydroxide); nordite (cerium lanthanum strontium calcium sodium manganese zinc magnesium silicate); octosilicate; pentagonite (hydrated calcium vanadate silicate); petalite (lithium aluminum silicate); prehnite (calcium aluminum silicate hydroxide); rhodesite (hydrated calcium sodium potassium silicate); sanbomite (barium silicate); serpentines such as antigorite (magnesium iron silicate hydroxide), clinochrysotile (magnesium silicate hydroxide), lizardite (magnesium silicate hydroxide), orthochrysotile (magnesium silicate hydroxide) and serpentine (iron magnesium silicate hydroxide); wickenburgite (hydrated lead calcium aluminum silicate); and zeophyllite (hydrated calcium silicate hydroxide fluoride).

In one preferred embodiment, the clay material is a phyllosilicate selected from the group consisting of clay minerals, kanemite, kenyaite, magadiite and makatite.

In another preferred embodiment, the phyllosilicate is a clay mineral, which is a group of phyllosilicates that contain a large percentage of water trapped between the silicate sheets. Most clay minerals are chemically and structurally analogous to other phyllosilicates but the larger amounts of water present, allow for more substitution of their cations.

Suitable clay minerals include chlorites such as baileychlore (zinc iron aluminum magnesium silicate hydroxide), chamosite (iron magnesium aluminum silicate hydroxide oxide), the generallized mineral chlorite, clinochlore (a chromium variety kaemmererite) (iron magnesium aluminum silicate hydroxide), cookeite (lithium aluminum silicate hydroxide), nimite (nickel magnesium iron aluminum silicate hydroxide), pennantite (manganese aluminum silicate hydroxide), penninite (iron magnesium aluminum silicate hydroxide) and sudoite (magnesium aluminum iron silicate hydroxide); glauconite (potassium sodium iron aluminum magnesium silicate hydroxide); illite (hydrated potassium aluminum magnesium iron silicate hydroxide); kaolinite (aluminum silicate hydroxide); montmorillonite (hydrated sodium calcium aluminum magnesium silicate hydroxide); palygorskite (hydrated magnesium aluminum silicate hydroxide); pyrophyllite (aluminum silicate hydroxide); sauconite (hydrated sodium zinc aluminum silicate hydroxide); talc (magnesium silicate hydroxide); and vermiculite (hydrated magnesium iron aluminum silicate hydroxide).

Swellable clay minerals are those that have alkali metals between their layers and can swell in polar solvents. These include lithium containing materials such as cookeite; sodium containing materials such as glauconite (which also contains potassium), montmorillonite and sauconite; and potassium containing materials such as illite. In some instances, such swellable materials are preferred over the non-swellable clay minerals.

It may be desirable to treat the phyllosilicate particles with an organic material to intercalate organic molecules between adjacent, planar silicate layers. For example, treatment can be with an organic material such as silane coupling agents; quaternary ammonium compounds; monomeric compounds having an electrostatic functionality selected from the group consisting of amines, amides and mixtures thereof; monomeric compounds having a functionality selected from the group consisting of hydroxyl, aromatic rings, carbonyl, carboxylic acid, polycarboxylic acid, aldehydes, ketones, amines, amides, ethers, esters and combinations thereof; an N-alkenyl amide monomer/allylic monomer combination, an oligomer formed by copolymerizing an N-alkenyl amide monomer and an allylic monomer, a polymer formed by copolymerizing an N-alkenyl amide monomer and an allylic monomer, and mixtures thereof; an intercalant polymer; and so forth.

In spite of some hydrophobization of the particle surface, such a treatment, for example by di(octadecyldimethyl)ammonium chloride or bromide, leads to distinctive separation of clay platelets and their homogeneous distribution in polymer matrix. The reinforcing clay particles typically have an average diameter of about <15μ, and the average diameter is preferably within the range of about 2-6μ. Their thickness is around 10-100 nanometers and therefore can be referred to as nanoparticles, and the composition is thus a "nanocomposite." Preferred clay particles are montmorillonite particles and are available from Southern Clay Products Co under the trademarks Cloisite Na+ (interspace length is 11.7 Å, Cloisite 15A (interspace length is 31.5 Å, clay modified with di(octadecyidimethyl)ammonium to render it more hydrophobic), Cloisite 20A, and so forth.

G. Optional Additives

The composition may also include conventional additives such as adhesive agents, antioxidants, crosslinking or curing agents, pH regulators, pigments, dyes, refractive particles, conductive species, antimicrobial agents, active agents and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the adhesive.

Adhesive Agents

The composition of the invention can also include additional adhesive agents that serve to improve the adhesive and tack properties of the adhesive, which is particularly beneficial to maintain adhesiveness when the skin-contacting adhesive is used in a manner such that it is subjected to a large amount of mechanical stress. Exemplary materials include tacky rubbers such as polyisobutylene, polybutadiene, butyl rubber, polystyrene-isoprene copolymers, polystyrene-butadiene copolymers, and neoprene (polychloroprene). Preferred adhesive agents include low molecular weight polyisobutylene and butyl rubber.

In one embodiment, a hydrophobic pressure-sensitive adhesive material is added, such as PIB, which tends to have a low surface energy (30.5 mJ/m$^2$) compared with SIS (35.0 mJ/m$^2$) and the fresh composition (32.5 mJ/m$^2$). Therefore, the PIB can readily migrate onto the patch surface. This migration can be accelerated by an extrusion procedure and/or by heating the patch, for example at 50° C. for 2 hours. After this treatment, the surface energy of the formulation becomes equal to 30.7 mJ/m$^2$, i.e., close to the PIB surface energy. Therefore, the inclusion of PIB in the contact zone with skin increases the initial tack.

A similar effect can be achieved by coating the patch surface with a dilute PIB solution in chloroform. After evaporation of solvent, the thin PIB layer forms reinforcing the initial tack without initiation of additional cold flow. Accordingly, the invention also contemplates coating the hydrophobic pressure-sensitive adhesive material onto the system and then heating the coating to remove any solvent and enable the material to diffuse into the system.

Antioxidants

The composition of the invention may also include one or more antioxidants, which may serve to enhance the oxidative stability of the composition. Heat, light, impurities, and other factors can all result in oxidation of the adhesive. Thus, ideally, antioxidants should protect against light-induced oxidation, chemically induced oxidation, and thermally induced oxidative degradation during processing and/or storage. Oxidative degradation, as will be appreciated by those in the art, involves generation of peroxy radicals, which in turn react with organic materials to form hydroperoxides. Primary antioxidants are peroxy free radical scavengers, while secondary antioxidants induce decomposition of hydroperoxides, and thus protect a material from degradation by hydroperoxides. Most primary antioxidants are sterically hindered phenols, and exemplary compounds for use herein are tetrakis [methylene(3,5-di-tert-butyl-4-hydroxyhydrocinnamate)]methane (e.g., Irganox® 1010, from Ciba-Geigy Corp., Hawthorne, N.Y.) and 1,3,5-trimethyl-2,4,6-tris[3,5-di-t-butyl-4-hydroxy-benzyl]benzene (e.g., Ethanox® 330, from Ethyl Corp.). Exemplary secondary antioxidants that may replace or supplement a primary antioxidant include tris(2,4-di-tert-butylphenyl)phosphite (e.g., Irgafos® 168, Ciba-Geigy Corp.). Other antioxidants, including but not limited to multifunctional antioxidants, are also useful herein and can serve as both a primary and a secondary antioxidant. Irganox® 1520 D, manufactured by Ciba-Geigy is one example of a multifunctional antioxidant. Vitamin E antioxidants, such as that sold by Ciba-Geigy under the tradename Irganox® E17, are also useful in the present adhesives. Other suitable antioxidants include, without limitation, ascorbic acid, ascorbic palmitate, tocopherol acetate, propyl gallate, butylhydroxyanisole, butylated hydroxytoluene, bis(1,2,2,6,6-pentamethyl-4-piperidinyl)-(3,5-di-tert-butyl-4-hydroxybenzyl)butylpropanedioate, (available as Tinuvin® 144 from Ciba-Geigy Corp.) or a combination of octadecyl 3,5-di-tert-butyl-4-hydroxyhydrocinnamate (also known as octadecyl 3-(3',5'-di-tert-butyl-4'-hydroxyphenyl)propionate) (available as Naugard® 76 from Uniroyal Chemical Co., Middlebury, Conn.) and bis(1,2,2,6,6-pentamethyl-4-piperidinylsebacate) (available as Tinuvin® 765 from Ciba-Geigy Corp.).

When included, the antioxidant can be present in amounts up to 2 wt % of the adhesive composition, but will typically be present in the range of about 0.05 wt % to 1.5 wt. %.

pH Regulators

Compounds useful as pH regulators include, but are not limited to, glycerol buffers, citrate buffers, borate buffers, phosphate buffers and citric acid-phosphate buffers. These regulators may be included so as to ensure that the pH of the composition is compatible with that of an individual's body surface.

Pigments, Dyes and Refractive Particles

Pigments, dyes and refractive particles are typically included in an adhesive for aesthetic purposes, either to mimic the coloration of the skin surface or to provide an otherwise colorful adhesive.

There are numerous pigments and/or dyes that can be included in the adhesive. Preferably such additives will not leach out and stain or otherwise irritate the skin surface. Refractive particles are particles that refract and reflect light striking the adhesive and the color of the reflected light changes as the angle at which the adhesive is viewed is changed. Exemplary refractive particles are those made from embossed, aluminized polyester.

Conductive Species

The composition may be rendered electrically conductive for use in biomedical electrodes and other electrotherapy contexts, i.e., to attach an electrode or other electrically conductive member to the body surface. For example, the adhesive may be used to attach a transcutaneous nerve stimulation electrode, an electrosurgical return electrode, or an EKG electrode to a patient's skin or mucosal tissue. Such applications generally involve modifying the adhesive composition so as to contain a conductive species, which renders the adhesive composition conductive. Suitable conductive species include those normally found in conductive adhesives used for application to the skin or other body surface, and include ionizable inorganic salts, organic compounds, or combinations of both. Examples of ionically conductive electrolytes include, by way of illustration and not limitation, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates, and combinations thereof. Although any amount of electrolyte may be present in the adhesive compositions of the invention, typically the electrolyte(s) will be present in an amount within the range of about 0.1-15 wt % of the adhesive.

Procedures for fabricating biomedical electrodes are well known in the art and can be readily adapted for incorporating the adhesive of the invention into such electrodes. See for example, U.S. Pat. No. 5,846,558 to Nielsen, et al., the disclosure of which is incorporated herein by reference with respect to manufacturing details.

Antimicrobial Agents

Antimicrobial agents may be included to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, proteins (i.e., lysozyme), silver salts, and combinations thereof.

Active Agents

One or more active agents can be included in the composition of the invention. Suitable active agents that may be incorporated into the adhesives of the invention, include the broad classes of compounds normally delivered through body surfaces and membranes such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In a preferred embodiment, the active agent is selected from the group consisting of antibiotics, antifungal agents, antiinflammatory agents, bacteriostatic and bactericidal compounds, caustic agents, keratolytic agents, pain relieving agents, proteolytic enzymes, tissue-healing enhancing agents, vasodilators, vessicants, and combinations thereof. Typically the active agent(s) will be present in a therapeutically effective amount. Examples of drugs within these classes are set forth below.

The release of active agents "loaded" into the adhesive of the invention typically involves both absorption of water and desorption of the agent via a swelling-controlled diffusion mechanism. Active agent-containing adhesives may be included in adhesive cushions, wound dressings, transdermal drug delivery devices and the like.

Antibiotics include antibiotics of the lincomycin family (referring to a class of antibiotic agents originally recovered from *Streptomyces lincolnensis*); antibiotics of the tetracycline family (referring to a class of antibiotic agents originally recovered from *Streptomyces aureofaciens*); sulfur-based antibiotics such as the sulfonamides; and so forth. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]amino]-1-thio-L-threo-α-D-galacto-octopyranoside), and pharmacologically acceptable salts and esters thereof. Exemplary antibiotics of the tetracycline family include tetracycline itself (4-(dimethylamino)-1,4,4α,5,5α,6,11,12α-octahydro-3,6,10,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Exemplary antifungal agents include chloroxylenol, ciclopirox, clotrimazole, griseofulvin, ketoconazole, miconazole, tolnaftate, undecylenic acid, and so forth.

Exemplary antiinflammatory agents include corticosteroids and nonsteroidal anti-inflammatory drugs. Examples of nonsteroidal anti-inflammatory drugs include alminoprofen, benoxaprofen, butibufen, carprofen, fenbufen, fenoprofen, flurbiprofen, ibuprofen, indoprofen, ketoprofen, naproxen, oxaprozin, pirprofen, pranoprofen, suprofen, tiaprofenic acid, and so forth.

Exemplary bacteriostatic and bactericidal compounds include, aryl mercury compounds such as phenylmercury borate or merbromin; alkyl mercury compounds such as thiomersal; chloramine; chlorhexidine; halogen compounds such as iodine, iodopovidone complexes (e.g., complexes of PVP and iodine, also referred to as "povidine" and available under the tradename Betadine® from Purdue Frederick); iodide salts; organic nitrogen compounds such as 8-hydroxyquinoline, chlorquinaldol, clioquinol, ethacridine, hexetidine, chlorhexedine and ambazone; organotin compounds such as tri-n-butyltin benzoate; oxidants such as hydrogen peroxide and potassium permanganate; phenols such as thymol, o-phenyl phenol, 2-benzyl-4-chlorophenol, hexachlorophen and hexylresorcinol; silver and silver-containing compounds such as sulfadiazine, silver protein acetyltannate, silver nitrate, silver phosphate, silver thiosulfate complex, silver acetate, silver lactate, silver sulfate and silver chloride and combinations thereof; sodium hypochlorite; zinc and zinc salts; and so forth.

Exemplary caustic agents include podophyllin, and the like.

Exemplary keratolytic agents include lactic acid, salicylic acid, urea, and so forth.

Exemplary pain relieving agents include local or topical anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and the like, with tetracaine, lidocaine and prilocaine being particularly suitable herein.

Exemplary proteolytic enzymes include those agents that are effective wound cleansing agents, and include, for example, pepsin, trypsin, collagenase, chymotrypsin, elastase, carboxypeptidase, aminopeptidase, and the like.

Tissue-healing enhancing agents are also referred to in the art as tissue regenerative agents and include agents such as collagen; glycosaminoglycans such as hyaluronic acid, heparin, heparin sulfate and chondroitin sulfate; proteoglycans such as versican and biglycan; peptides such as fibronectin, vitronectin, osteopontin and thrombospondin, all of which contain the tripeptide sequence RGD (arginine-glycine-aspartic acid), a sequence generally associated with adhesive proteins and necessary for interaction with cell surface receptors; polypeptide growth factors such as platelet-derived growth factor, fibroblast growth factor, transforming growth factor and insulin-like growth factor; substrate adhesion molecules such as fibronectin, vitronectin and laminin; and so forth.

Exemplary vasodilators include those topical vasodilators useful for increasing blood flow in the dermis, such as rubefacients and counterirritants. Rubefacient agents include nicotinic acid, nicotinates such as methyl, ethyl, butoxyethyl, phenethyl and thurfyl nicotinate, as well as the essential oils such as mustard, turpentine, cajuput and capsicum oil, and components thereof.

Exemplary vessicants include cantharidin, and the like.

Permeation Enhancers

One or more permeation enhancers can be included in the composition of the invention. With some active agents, it may be desirable to administer the agent along with a suitable permeation enhancer in order to achieve a therapeutically effective flux through the skin or mucosa. Selection of suitable permeation enhancers will depend upon the agent being delivered, as well as the enhancer's compatibility with the other components of the adhesive.

Exemplary permeation enhancers include, by way of illustration and not limitation, sulfoxides such as dimethylsulfoxide and decylmethylsulfoxide; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan-2-one; alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

Water-Swellable Water-Insoluble Polymers

When the compositions of the invention are used as a slowly dissolving film, for example, containing one or more active agents, it may be desirable to also include a water-swellable water-insoluble polymer, along with the hydrophilic polymer, complementary polymer, and clay particles.

Exemplary water-swellable water-insoluble polymers are acrylate-based polymers or copolymers, generally formed from acrylic acid, methacrylic acid, methyl acrylate, ethyl acrylate, methyl methacrylate, ethyl methacrylate, and/or other vinyl monomers. Several of these are also classified as hydrophilic polymers, above. Suitable acrylate polymers are those copolymers available under the tradename "Eudragit" from Rohm Pharma (Germany). The Eudragit® series E, L, S, RL, RS and NE copolymers are available solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L 30D-55 and Eudragit L 100-55 (the latter copolymer is a spray-dried form of Eudragit L 30D-55 that can be reconstituted with water). The molecular weight of the Eudragit L 30D-55 and Eudragit L 100-55 copolymer is approximately 135,000 Da, with a ratio of free carboxyl groups to ester groups of approximately 1:1. The Eudragit L 100-55 copolymer is generally insoluble in aqueous fluids having a pH below 5.5. Another particularly suitable methacrylic acid-methyl methacrylate copolymer is Eudragit S-100, which differs from Eudragit L 30D-55 in that the ratio of free carboxyl groups to ester groups is approximately 1:2. Eudragit S 100 is insoluble at pH below 5.5, but unlike Eudragit L 30D-55, is poorly soluble in aqueous fluids having a pH in the range of 5.5 to 7.0. This copolymer is soluble at pH 7.0 and above. Eudragit L 100 may also be used, which has a pH-dependent solubility profile between that of Eudragit L 30D-55 and Eudragit S 100, insofar as it is insoluble at a pH below 6.0. It will be appreciated by those skilled in the art that Eudragit L 30D-55, L 100-55, L 100, and S 100 can be replaced with other acceptable polymers having similar pH-dependent solubility characteristics. Other suitable acrylate polymers are those methacrylic acid/ethyl acrylate copolymers available under the tradename "Kollicoat" from BASF AG (Germany). For example, Kollicoat MAE has the same molecular structure as Eudragit L 100-55.

H. Additional Elements

Backing Member

The composition of the invention may be formulated so as to include a backing member, which can be laminated to the composition to serve as the outer surface of a dressing, cushion or transdermal drug delivery device following application to the skin. Exemplary backing member materials include fibrous or porous sheet materials such as flannel, felt, cotton, polyesters, polyethylene, polypropylene, polyurethanes, polyether amides and the like. The backing member is typically along the order of about 1-2.5 mils in thickness, but may be thinker or thinner as needed. If desired, the backing can be pigmented, metallized, or provided with a matte finish suitable for writing.

The backing layer may be non-occlusive (or "breathable"), i.e., permeable to moisture and will generally be made of a flexible, resilient outer layer, fabricated from a translucent or transparent, film, a foam pad or fibrous material such as fabric, with a layer of the adhesive composition of the invention laminated thereto for application to the skin surface. Exemplary backing players include transparent polyurethane, transparent polyurethane coated with acrylic adhesive (to reinforce the connection between the adhesive composition and backing layer and foamed polyurethane. Use of foamed or fabric backings may provide for increased cushioning, however, use of such as backing will decrease the transparency properties of the product. When moisture permeability is particularly preferred, the backing layer should provide for anisotropic moisture transportation, i.e., from the skin through the composition and the backing member, and then to the environment, but not vice versa, for example during bathing.

In general, the material used for the backing layer should permit the composition to follow the contours of the skin and be worn comfortably on areas of skin such as at joints or other points of flexure, that are normally subjected to mechanical strain with little or no likelihood of the adhesive disengaging from the skin due to differences in the flexibility or resiliency of the skin and the adhesive.

Since the backing member covers a large surface area of the composition, a highly water permeable backing can serve as a significant conduit for water to enter the adhesive. The combination of the degree of water permeability into the backing and the ability of the adhesive o hold water for a required period of wearing time needs to be in balance. Thus if the adhesive is designed to hold enough water from the skin and from the periphery of the adhesive and not lose its cohesive-adhesive properties during the required period of wearing time, then a water impermeable backing is suitable for use.

However, if it is preferred to have some water leave the adhesive during wearing then a water or moisture permeable backing is preferred. In that instance, the amount of water intrusion into the adhesive and the moisture vapor transmission rate should be balanced. Also water should not be too soluble in the backing layer otherwise the backing layer may swell and either delaminate or cause the adhesive to lift-off prematurely. The outer surface of the backing ideally has a surface property that minimizes the ability of the adhesive to grab cloth normally used in socks, stockings or bed linen.

When the composition is used in a dressing or cushion, the backing is preferably able to conform to the skin surface to which it is applied, for example, it can conform to the curvature of the ball and heel of a human foot when the foot is at rest. During walking or running there will be intermittent increased compression, tension and shear forces on the backing and the adhesive. Use of a flexible and/or elastic backing member, minimizes the occurrence of adhesive residue beyond the perimeter of the backing, which then would cause the dressing or cushion to stick to socks or bed coverings and possibly become detached from the skin surface. Thus the coefficient of friction, compression and other elastic properties of the backing are also important considerations.

In one embodiment of the invention, the backing is a polyurethane film having a thickness of about 1.5-2.0 mils. In another embodiment of the invention, the backing is a polymeric foam material. The porous nature of the foam can provide a depot of adhesive so that as pressure is applied to the skin-contacting adhesive, the adhesive formulation is continuously forced out of the pores to replenish the adhesive layer that is in contact with the skin.

Release Liner

The composition of the invention may be formulated so as to include a release liner, which can serve to protect the composition during storage and prior to use. The release liner preferably peels away with an easy peel and does not stick aggressively nor become difficult to remove from the composition during storage. Ideally, the release liner has adhesive properties that remain contact over time. The release liner can be made from numerous suitable materials, but is preferably differentiated from the composition of the invention, cushion, etc., by material texture or design and is impermeable to the composition. Exemplary release liners include silicone or fluorocarbon treated materials, polyesters, polyvinyl chloride, cellulose acetate, polypropylene, polyethylene and polyethylene terephthalate films. The release liner is typically along the order of about 3 mils in thickness, but may be thinker or thinner as needed.

Applicator Tab or Mechanism

The composition of the invention may be formulated so as to include an applicator tab or applicator mechanism, which is designed to facilitate application of the adhesive, cushion, etc., to the appropriate skin location. For example, an applicator tab can be a 2 mil polyolefin film.

III. Configuration and Size

The skin contact area of the composition of the invention may be any size, but will typically be within in the range of about 3-250 $cm^2$, and preferably in the range of about 20-150 $cm^2$, depending on the specific application as described in part V below.

IV. Fabrication

The composition of the invention is melt extrudable, and thus may be prepared using a simple blending and extruding process. The components of the composition are weighed out and then admixed, for example using a Brabender, Haake or Baker Perkins Blender, generally at a temperature within the range of about 90-160° C. Solvents may be added, but are not required. The resulting composition can be extruded using a single or twin-screw extruder. The composition can be extruded directly onto a substrate such as a backing member, covered with a release liner, profiled, and then cut. Another possibility consists in extruding a thin layer of the formulation between two release liners with subsequent cutting and pressing, using, for example, a Carver press.

The resulting composition can have a variety of thicknesses, but typically will be in the range of about 0.10-1.0 mm, more usually in the range of about 0.20-0.60 mm. In a preferred embodiment, the composition is configured to have a tapered edge.

The order in which the various ingredients may be added into the mixer is not critical to the invention. However, in a preferred method, the clay particles are mixed with the complementary polymer, prior to mixing with the other ingredients to reach a uniform distribution. In addition, it may be desirable to intercalate the clay structure with components such as di- or polyglycols, by first mixing the clay particles with such components prior to adding the clay to the formulation. In another preferred method, a pre-mixture of the hydrophilic polymer, the complementary polymer, and the clay particles, is formed. To this pre-mixture, is added the hydrophobic polymer, the tackifying resin, additional clay particles, and finally the elastomeric plasticizer.

The temperature may be increased or decreased with each addition to facilitate manufacture or to control the product characteristics. For example, certain components can be added at lower temperature to prevent their possible chemical decomposition. In this manner, the physical characteristics of the composition can be modified by altering the temperature regime, agitation speed and time.

The temperature profile can also be designed to provide for a desirable consistency of the composition so that one is able to press the formed edge and to cut the desired wound dressing, mucosal, or cushion product. A suitable temperature for fabrication is around 70-110° C.

V. Specific Uses

The compositions of the invention find utility in numerous applications, such as in transdermal and/or transmucosal drug delivery devices, topical and transdermal pharmaceutical formulations, pressure-relieving cushions (which may or may not be medicated), bandages, ostomy devices, prosthesis securing means, face masks, sound, vibration or impact absorbing materials, and the like. Also, the compositions may be rendered electrically conductive by incorporation of an electrically conductive material, and may thus be used for attaching an electroconductive particle, such as an electrode (e.g., a transcutaneous electric nerve stimulation electrode, an electrosurgical return electrode or an EKG monitoring electrode), to an individual's body surface.

The compositions provide several significant advantages, including:
(1) fabricated so as to be translucent, which enables one to view the extent of wound healing without removing the formulation from the body surface;
(2) display very high swelling upon contact with water;
(3) contain nanospaces to store the active agents and release them under the appropriate conditions;
(4) exhibit little or no cold flow during use; and
(5) are readily modified during manufacture so that properties such as adhesion, absorption, and translucence can be optimized.

A. Adhesive Cushion

The compositions of the invention are useful in any number of applications wherein adhesion of a product to a body surface is called for or is desirable. One such embodiment is an adhesive cushion which comprises a skin-contacting layer of the composition of the invention, and a backing layer as described above.

Suitable cushions include, arch support pads, blister pads, bunion pads, callus pads, corn pads, elbow pads, finger pads, forearm pads, heel cushions, insoles, knee pads, metatarsal pads, shin pads, toe pads, wrist pads, and so forth. Preferably, the adhesive cushion stays affixed to the skin for at least seventy-two hours.

The adhesive cushion may further comprise a therapeutically effective amount of an active agent, as defined above. In particular, active agents such as bacteriostatic and bactericidal compounds and antibiotic agents, and combinations thereof may be included in the adhesive composition.

The adhesive cushion can have a skin-contacting area in the range of about 3-250 $cm^2$, typically about 3-10 $cm^2$. A common shape for adhesive callus cushions is circular, and such patches will typically have a diameter within the range of about 3.15-3.50 cm. Blister, bunion and corn cushions typically have an elliptic shape with tapered edges of different dimensions.

The adhesive cushion finds particular utility as pressure-relieving cushion for application to a foot. In one such embodiment, the cushion contains an active agent for the treatment of dicubitis, veinous and diabetic foot ulcers, or the like.

B. Wound Dressings

The compositions of the invention are useful as wound dressing. An exemplary wound dressing comprises a laminated composite of a body facing layer having a body-contacting surface, and an outwardly facing non-occlusive backing layer, wherein at least a portion of the body-contacting surface is comprised of the adhesive composition of the invention.

For wound dressings, suitable active agents are those useful for the treatment of wounds, and include, but are not limited to antibiotics, antifungal agents, antiinflammatory agents, bacteriostatic and bactericidal compounds, pain relieving agents, proteolytic enzymes, tissue-healing enhancing agents, vasodilators, and combination thereof. Specific agents within these classes are set above.

The wound dressing can be designed such that the entire body-contacting surface is comprised of the adhesive, or the perimeter can be made up of the adhesive with an inner wound-contacting region made of a material such as a hydrogel or a non-tacky hydrocolloid with a high moisture adsorption capacity (matrix-island design). The wound dressing may further include a backing layer and a removable release liner that covers and is co-extensive with the body-facing surface of the wound dressing.

It may be desirable to prepare the adhesive composition so that it is substantially nontacky, or at most slightly tacky, when applied to the body surface. In addition, the adhesive composition may further comprise a therapeutically effective amount of an active agent, as defined above, that is suitable for application to a wound. In particular, active agents such as antibiotics, antifungal agents, antiinflammatory agents, bacteriostatic and bactericidal compounds, pain relieving agents, proteolytic enzymes, tissue-healing enhancing agents, vasodilators, and combination thereof may be included in the adhesive composition.

A typical skin-contacting area in the range of about 3-250 $cm^2$, typically about 3-10 $cm^2$. Wound dressings are often rectangular in shape, and are commonly as large as 250 $cm^2$.

C. Transdermal Drug Delivery Devices

The skin-contacting adhesive composition also find utility when incorporated into a transdermal drug delivery device.

One exemplary device comprises a drug reservoir containing a therapeutically effective amount of an active agent, an outwardly facing backing layer, and a means for affixing the device to a body surface comprising the adhesive composition of the invention.

In the manufacture of such transdermal drug delivery devices, the skin-contacting adhesive composition may be cast or extruded onto a backing layer or release liner of such a device and will serve as the skin contacting face of the "patch." The drug reservoir may be separate from the adhesive composition or the adhesive itself may be serve as a drug reservoir within the device.

Any number of active agents can be administered using these drug delivery devices of the invention. The device will contain a quantity of a pharmacologically active agent effective to provide the desired dosage over a predetermined delivery period and may also contain a carrier (e.g., a vehicle to solubilize the active agent), a permeation enhancer, if necessary, and optional excipients such as colorants, thickening agents, stabilizers, surfactants and the like.

The transdermal drug delivery device may also contain a release liner or a rate-controlling membrane formed of a material selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like. If a specific drug can interspersed within the clay crystalline structure, in the presence of moisture, the drug will be releases according to the laws of diffusion. This process will be accompanied by the exchange of charged species inside the clay interspaces, thus providing a constant drug release rate.

D. Oral Care Products

The adhesive compositions of the invention are also useful in formulating a variety of oral care products. They are useful, for example, to provide products which allow topical administration of a variety of active ingredients for the treatment of conditions of the mouth such as infection, inflammation, cold sores, cankers, traumatic injuries, or gingivitis. These active agents may include as active ingredients, for example, antibiotics, antiinflammatory drugs, pain relieving agents, proteolytic enzymes, and tissue healing enzymes, for example of the types listed above in part II.G. A composition containing as an active agent triclosan, for example, may be used as an anti-gingivitis formulation. The active agent for an oral care formulation employing the adhesive compositions of the invention may also be a breath-freshening, tooth-coloring, or other cosmetic agent. Oral care formulations employing the adhesive compositions of the invention may be designed to contain multiple active ingredients either in a single component or in different components which make up the oral care formulation. For example, the multiple active ingredients may be disposed in different layers in addition to the adhesive layer which is in immediate contact with the teeth or some other surface within the oral cavity. Alternatively, there may be two or more components side by side each containing different active ingredients.

The adhesive compositions of the invention are useful in particular in tooth whitening products. Much information about the design of tooth whitening products is found in U.S. Published patent application No. 2004/0105834 to Singh et al.

An exemplary oral care product which can be made with the adhesive compositions of the invention comprises a flexible strip of adhesive-containing material that is applied across a row of teeth. This oral care product comprises an outer backing member that provides the external surface of the system following application to the teeth; one or more actives (for example, tooth whitening or anti-gingivitis actives) in an adhesive layer which is in contact with the outer backing member; and a removable release liner as described above that covers the otherwise exposed active-containing adhesive composition prior to use. The backing member may be as described above in part II.G. It may be composed of an inert material, e.g., polyester, polyethylene, polypropylene, polyurethane, or the like. Ideally, the backing is relatively soft and flexible so as to permit the system to conform to the contour of the teeth and minimize any discomfort to the user. The backing member may itself contain active ingredients.

Other oral care products made with the adhesive formulations of the invention may be designed to adhere to other portions of the oral cavity, for example to the gums, the palate, or the area surrounding the lips.

The adhesive compositions of the invention may be designed to dissolve or erode after a certain period of time in contact with the moisture of the mouth, as discussed above. They may consequently be employed in oral care products which dissolve or erode in the mouth, and so do not have to be removed by the user. Such oral care products may be used to deliver the active ingredients listed above. In the formulation of such products which include a backing member, it is desirable that the backing member erode more slowly than the medium which adheres to the teeth or other oral surfaces. The design of such backing members is discussed in U.S. Published patent application No. 2004/0105834, cited above. A preferred class of such backing members is made out of acrylate polymers. Preferred acrylate polymers are the Eudragit® copolymers (copolymers of methacrylic acid and methyl methacrylate), such as the Eudragit® series E, L, S, RL, RS and NE copolymers. In addition, mixtures of Eudragit polymers or mixtures of Eudragit polymers with other polymers and excipients (e.g., buffering agents, pH modulators) may be used to tailor the rate of erosion of the backing member relative to the remaining components of the oral care product.

E. Other Products Requiring Adhesion to Body Surfaces

The compositions of the invention are also useful in a host of other contexts, e.g., as adhesives for affixing medical devices, diagnostic systems and other devices to be affixed to a body surface, and in any other application wherein adhesion to a body surface is necessary or desired. The compositions are also useful as sealants for ostomy devices, as prostheses including dental adhesives, as face masks, as sound, vibration or impact absorbing materials, as carriers in cosmetic and cosmeceutical gel products, slowly dissolving films containing drugs or breath fresheners for oral application, and will have other uses known to or ascertainable by those of ordinary skill in the art, or as yet undiscovered.

The practice of the present invention will employ, unless otherwise indicated, conventional techniques of polymer chemistry and adhesive manufacture, which are within the skill of the art. Such techniques are fully explained in the literature.

EXAMPLES

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

| ABBREVIATIONS AND TRADEMARKS | |
|---|---|
| The following abbreviations are used in the examples: | |
| Cloisite Na+ | Natural clay (Southern Clay Products) |
| Cloisite 15A | Natural clay modified with dioctadecylammonium (Southern Clay Products) |
| Eudragit | Eudragit 100-55, methacrylic acid copolymer (Rohm America Inc.) |
| HPC | Hydroxypropylcellulose (Hercules) |
| Irganox | Irganox ®1010, tetrakis [methylene (3,5-di-tert-butyl-4-hydroxyhydrocinnamate)] methane (Ciba-Geigy) |
| Isolene | Isolene ®400, cis-1,4 polyisoprene (Elementis Specialties Performance Polymers) |
| PEG | PEG 400, a polyethylene glycol |
| 1,2-PG | 1,2-propyleneglycol |
| PIB | Polyisobutylene, Vistanex ®LM-MH (ExxonMobil Chemical) |
| PVP | Kollidon ®90 polyvinylpyrrolidone (BASF) |
| Regalite | Regalite ®9100, a partially hydrogenated hydrocarbon resin (Hercules) |
| SIS | SIS Vector 4114, a styrene-isoprene-styrene block copolymer (Dexco Polymers); 42 wt % styrene-isoprene diblock; overall styrene:isoprene ratio of 15:85 |

Example 1

Formulation 1 was made as follows. To 21 g of PEG, 7 g of Cloisite Na+ was added and mixed by hand until homogeneous paste was formed. Part of the powdered PVP was added to this paste until handling was possible. The resulting premix was transferred to a Haake mixer with two sigma-bladed rotors, heated to 130° C. The remainder of the PVP was added by small portions during 12 min at an agitation rate of 30 rpm. The mixing of the formulation as whole continued for 60 min. The final composition is shown in Table 1.

TABLE 1

| Ingredients | Total amount (g) | Wt % of total |
|---|---|---|
| PVP | 42.0 | 60.0 |
| PEG | 21.0 | 30.0 |
| Cloisite Na+ | 7.0 | 10.0 |

The hydrogel Formulation 1 is transparent, rather rigid and can be dissolved in water. This formulation can be worn on a body surface without prominent squeezing. The cold flow was significantly less than for similar PVP-PEG compositions, a feature possibly attributable to the intercalation of PEG and clay, which hinders its mobility. To prove this hypothesis, an X-ray diffraction pattern was obtained, which indicated a shift of the basal reflection of clay to smaller angles, i.e., an increase of interspace distance. The loss of molecular mobility decreased the dissolution time of the PVP-PEG formulation ~1.3 times. While a promising candidate for mucosal application, the formulation would preferably be modified to increase dissolution time.

Example 2

In order to increase the dissolution time, the interaction between polymer components must be much higher. PVP and PEG are able to form H-bonds between terminal hydroxyl groups of PEG and carbonyl groups of PVP. This interaction leads to formation of a rather rare physical network that prevents fast dissolution. This additional delay of dissolution permits the intercalation process to occur. To increase the density of H-bonds, PEG was substituted by low molecular weight 1,2-PG, and additional components were introduced containing carboxy-groups (Eudragit) or hydroxyls (HPC). As a result, two other formulations, Formulations 2 and 3, were prepared, as shown in Table 2.

TABLE 2

| Ingredients | Formulation 2, wt % of total | Formulation 3, wt % of total |
|---|---|---|
| PVP | 58.0 | 58.0 |
| PEG | 28.0 | 28.0 |
| Cloisite Na+ | 2.0 | 2.0 |
| Eudragit | 12.0 | — |
| HPC (MW = 1,150,000) | — | 12.0 |

The mixing procedure was as follows. Powdered PVP was added to liquid 1,2-PG until a viscous mass was formed. Clay particles were dispersed in this mass by hand. The mass was then transferred to a Haake mixer, heated to 130° C. at an agitation speed of 30 rpm, and residual PVP and Eudragit (or HPC) was added by small portions with interval of 6-7 min. The total mixing circle was ~60 min. The final formulations were clear and could be easily processed into samples with a thickness of ~0.3 mm by hot pressing. They were tested as blisters and as slowly dissolving films. For blister application these compositions were worn for 24-36 hours. The compositions showed good potential for use as slowly dissolving films. Formulation 2 was worn on the oral mucosa (arch and cheek) for 30-90 min, providing a swollen film that had dissolved a little and formed gel. The film was removed without leaving any residue on the mucosal surface. Formulation 3 dissolved completely upon oral application, with a dissolution time of >20 min.

Example 3

To improve the resistance that adhesives develop to loading, e.g., by body weight, the selected hydrogel formulation was combined with a hydrocolloid matrix. For this purpose several formulations were prepared containing an SIS-based matrix and a high content of the hydrophilic phase, Formulations 4-7, shown in Table 3.

The first stage was prepared as a PVP/PEG/clay composition as a pre-mixture (PM). To 21 g of PEG, 7 g of Cloisite Na+ or Cloisite 15A was added and mixed by hand until it reached a relatively homogeneous dispersion, approximately 5 minutes. During this stage, PEG penetrates into the clay interspaces. This dispersion was then placed in a Haake mixer with sigma-blades (Benbary rotors can be used in place of the sigma-blades) at 30 rpm. 42 g of PVP powder was then slowly added, over a period of approximately 40 minutes, at room temperature and 30 rpm. Therefore, the PM contained 60% PVP, 30% PEG, and 10% clay.

Due to the high viscosity of the pre-mixture composition, the temperature increased to about 50-60° C. as a result of self-heating. The mixing continued for approximately 85 minutes at a rotor speed of 60 rpm. After the pre-mixture was prepared, the mixer was discharged. For all final hydrocolloid formulations the temperature regime of mixing was similar.

TABLE 3

| Ingredients | Formulation 4, wt % | Formulation 5, wt % | Formulation 6, wt % | Formulation 7, wt % |
| --- | --- | --- | --- | --- |
| SIS | 20.0 | 20.0 | 20.0 | 20.0 |
| Regalite | 13.5 | 17.0 | 17.0 | 17.0 |
| Isolene | 15.0 | 15.0 | 15.0 | 15.0 |
| PIB Vistanex LM-MH | 10.0 | 10.0 | 10.0 | — |
| Paraffin oil | 3.5 | — | — | — |
| Clay Cloisite Na+ | — | — | — | 8.0 |
| Clay Cloisite 15A | — | — | 4.0 | — |
| Irganox | 0.1 | 0.1 | 0.1 | 0.1 |
| PM | 38.0 | 38.0 | 34.0 | 40.0 |

The mixing regime for Formulation 7 was as follows. The temperature was increased to 130° C. and 14 g of SIS and 11.9 g of Regalite was added at 30 rpm. After approximately 15 minutes after the start of mixing, 28 g of the PM was added (containing approximately 16.8 g PVP, 8.4 g PEG, and 2.8 g clay). After approximately 15 minutes, 5.6 g of additional clay was added. After about 10 minutes, 10.5 g of Isolene was introduced. After charging this last ingredient, the speed was increased to 60 rpm and the mixing continued for another 30 minutes.

The composition was pumped from the mixer and extruded on a release liner or other appropriate substrate.

Formulation 7, and commercial products DuoDERM® Control Formula Dressing ("DuoDERM CGF") and DuoDERM® Extra Thin CGF® Dressing ("DuoDERM Thin"), both from ConvaTec Ltd., were tested for their adhesion force to a PET or PE substrate and also to human skin. The results on adhesion strength to PET and PE substrates, as well as the moisture vapor transmission rate and water uptake are presented in Table 4.

TABLE 4

| Formulation | Adhesion relatively PET/PE, N/m and character of failure | MVTR, g/m²/24 h at 20/37° C. | Water uptake, wt/wt %, at 32° C. |
| --- | --- | --- | --- |
| 7 (16.5 mil) | 308/205 (adhesion) | 165.4/215 | 64.4/1.81 |
| DuoDERM CGF | 285/165 (cohesion) | 7/42.5 | 58.1/1.39 |
| DuoDERM Thin | 298/147.5 (cohesion) | 19.2/96.2 | 41.4/0.71 |

Formulation 7, as well as Formulations 5 and 6 in the table below, were prepared by melt mixing and pressing (or extrusion). All formulations had the same design: a backing film Medifilm 437 (non-tacky) with a thickness of 1.5 mil, an adhesive layer (~15 mil), and a release liner (PET film with one anti-adhesion side). Compared with the DuoDERM dressings, Formulation 7 had several important advantages: MVTR and water uptake were essentially higher at approximately the same values of adhesion strength to both substrates.

Data on peel force relative to human skin are shown in Table 5. Peel force was measured at a 180° direction of peel force action as a function of the wearing time.

TABLE 5

| | Time, h | | | |
| --- | --- | --- | --- | --- |
| Formulation | 0.3 | 24 | 48 | 72 |
| 5 | 133 | 50 | 17 | |
| 6 | 121 | 83 | 58 | |
| 7 | 38-M | 142-M | | |
| | 38-M | 271-M | | |
| | 67-M | 350-M | | |
| | 54-F | 358-F | 233-F | 200-F |
| DuoDERM CGF | 30-M | 50-M | | 58-M |
| | 36-F | 61-F | | 50-F |
| | 55-M | 46-M | | |

The most unusual feature of Formulation 7 is the increase of adhesion in wearing time. For two categories of volunteers (M=male, F=female), the peel force after 24 hours of wearing was 4-7 times higher than the initial peel force. For other formulations including the DuoDERM CGF dressing, such an effect was not observed. Formulations 4-6 also did not show this effect, presumably due to the presence of 10% of PIB, which formed a hydrophobic layer at extrusion, which served to decelerate the rate of moisture stream. An explanation of this effect is based on the dependent of adhesion strength on water content for PVP-PEG compositions. Due to an increase of free volume and the change of rheological properties in the presence of water, the adhesion strength of this pair of polymers has a maximum. The maximum of adhesion strength corresponds to ~20 wt % of water, i.e., in 24 hours the water concentration in Formulation 7 reaches this value. Upon further moistening, the peel force decreases. This formulation can be used for prolonged application on full- or partial-thickness wet wounds or as a matrix for matrix-island dressings, or as a blister patch. Formulations 4-6 will find utility as corn and bunion cushions, blister patches, dressings for accusative wounds, and so forth. The results of a wearing study of the blister patch prepared from Formulation 7, as compared to a blister patch sold under the brand name Dr. Scholl's (Schering-Plough HealthCare Products Inc.), are presented in Table 6. Six volunteers were used in the study.

TABLE 6

| Sample: | Formulation 7 (10 mils) | | | Formulation 7 (15 mils) | | | Dr. Scholl | | |
|---|---|---|---|---|---|---|---|---|---|
| Elapsed Time (hr) | 66.5 | | | 68.0 | | | 57.1 | | |
| # of Showers | 2.2 | | | 2.4 | | | 2.8 | | |
| | Initially | Day 2 | Day 3 | Initially | Day 2 | Day 3 | Initially | Day 2 | Day 3 |
| Adhesion | 4.0 | — | — | 4.0 | — | — | 3.8 | — | — |
| Slippage | 4.0 | 4.0 | 3.4 | 4.0 | 4.0 | 3.4 | 3.8 | 2.8 | 2.3 |
| Edge Lift | 4.0 | 3.0 | 1.8 | 4.0 | 3.6 | 2.8 | 3.8 | 2.0 | 1.3 |
| Comfort | 4.0 | 4.0 | 3.2 | 4.0 | 4.0 | 3.2 | 3.8 | 2.8 | 2.0 |
| Cold Flow | 4.0 | 4.0 | 3.2 | 4.0 | 4.0 | 3.2 | 3.8 | 2.5 | 2.0 |

The durability of wearing was observed to be higher for Formulation 7. When properties such as initial tack, slippage, edge lift, comfort, cold flow, were estimated on a 4-grade scale, they were much higher for Formulation 7 than for the Dr. Scholl products, especially for days 2 and 3. The patch thickness was not found to have a significant effect on the wearing results, although the data for the 15 mil (~375μ) patch was slightly better than for the 10 mil patch.

Example 4

Formulations 8-10 were developed for use as a non-tacky island, capable of absorbing a significant amount of moisture. In order to increase water uptake, additional hydrophilic agents such as HPC and agar were introduced to the formulation. In addition, hydrophilic clay Cloisite Na+ contained in the PM was used in combination with more hydrophobic Cloisite 15A, modified with dioctadecyldimethyl ammonium bromide. In general, HPC, agar and clay were found to suppress the initial tack and adhesion strength. In addition, the adhesion promoter Regalite and low molecular weight PIB were removed. The resulting formulations are presented in Table 7.

TABLE 7

| Ingredients | Formulation 8 | Formulation 9 | Formulation 10 |
|---|---|---|---|
| SIS | 10.0 | 15.0 | 20.0 |
| Isolene | 10.0 | 20.0 | 10.0 |
| HPC (MW = 850,000) | 20.0 | 25.0 | 10.0 |
| Agar | 40.0 | — | 10.0 |
| PM | 20.0 | 40.0 | 35.0 |
| Clay Cloisite 15A | — | — | 15.0 |

These formulations exhibited a very high swell ratio calculated as the weight of the swollen sample over the weight of the dried sample, as much as 20-fold. The formulations could also be pressed together without showing a distinctive boundary. The wearing results of matrix-island patches on healthy hand skin were successful, with the wear time exceeding 80 hours in 60% of wearers and exceeding 100 hours for 20% of wearers.

All patents, patent applications, journal articles and other references cited herein are incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

Accordingly, the scope of the invention should therefore be determined with reference to the appended claims, along with the full range of equivalents to which those claims are entitled.

We claim:

1. An adhesive composition comprising:
   a hydrophobic polymer selected from polyisobutylenes, butyl rubbers, natural rubber adhesives, vinyl ether polymers, polysiloxanes, polyisoprenes, styrene-isoprene-styrene block copolymers, styrene-butadiene-styrene block copolymers, isobutylene-isoprene copolymers, butadiene acrylonitrile rubber, polychloroprenes, ethylene-propylene-diene terpolymers, acrylates, and combinations thereof;
   an elastomeric plasticizer;
   a tackifying resin;
   a hydrophilic polymer selected from poly(N-vinyl lactams), poly(N-vinyl amides), poly(N-vinyl acrylamides), poly(N-alkylacrylamides), polyacrylic acids, polymethacrylic acids, polyvinyl alcohol, polyvinyl amine, and copolymers and blends thereof;
   a third polymer capable of hydrogen bonding to the hydrophilic polymer, and clay particles comprised of a water-swellable clay mineral.

2. The composition of claim 1, wherein the hydrophobic polymer is selected from polyisoprenes, butyl rubbers styrene-isoprene-styrene block copolymers, and styrene-butadiene-styrene block copolymers.

3. The composition of claim 1, wherein the elastomeric plasticizer is selected from styrene-based plasticizers, polyisobutylenes with molecular weight 20,000-100,000, polyisoprene rubbers with molecular weight 20,000-100,000, and combinations thereof.

4. The composition of claim 3, wherein the styrene-based plasticizer is selected from styrene-butadiene block copolymers, styrene-isoprene block copolymers, and combinations thereof.

5. The composition of claim 1, wherein the hydrophilic polymer is selected from poly(N-vinyl lactams), poly(N-vinyl amides), poly(N-alkylacrylamides), and copolymers and blends thereof.

6. The composition of claim 1, wherein the third polymer is an oligomer having a molecular weight in the range from 45 to 800 selected from polyalkylene glycols, polyalcohols, monomeric and oligomeric alkylene glycols, ether alcohols, carbonic diacids, and alkane diols.

7. The composition of claim 6, wherein the oligomer is a polyalkylene glycol.

8. The composition of claim 1, wherein the clay particles have an average diameter of <15μ.

9. The composition of claim 1, which comprises about 1-40 wt % hydrophobic polymer; about 1-30 wt % elastomeric plasticizer; about 1-30 wt % tackifying resin; about 1-50 wt % hydrophilic polymer; about 1-30 wt % third polymer, and about 1-30 wt % clay particles, percentages being with respect to the entire composition.

10. The composition of claim 9, which comprises about 15-25 wt % hydrophobic polymer; about 10-20 wt % elastomeric plasticizer; about 13-20 wt % tackifying resin; about 20-30 wt % hydrophilic polymer; about 8-18 wt % third polymer; and about 8-15 wt % clay particles.

11. The composition of claim 1, which further comprises an active agent.

12. The composition of claim 11, wherein the active agent is selected from antibiotics, antifungal agents, antiinflammatory agents, bacteriostatic and bactericidal compounds, caustic agents, keratolytic agents, pain relieving agents, proteolytic enzymes, tissue-healing enhancing agents, vasodilators, vessicants, and combinations thereof, and is present in a therapeutically effective amount.

13. The composition of claim 11, which further comprises a permeation enhancer.

14. The composition of claim 1, which further comprises at least one additive selected from the group consisting of adhesive agents, antioxidants, crosslinking or curing agents, pH regulators, pigments, dyes, refractive particles, conductive species and antimicrobial agents.

15. An adhesive composition comprising:
a hydrophobic polymer selected from polyisoprenes, butyl rubbers styrene-isoprene-styrene block copolymers, and styrene-butadiene-styrene block copolymers;
an elastomeric plasticizer selected from styrene-based plasticizers, low molecular weight polyisobutylenes, low molecular weight polyisoprene rubbers, and combinations thereof;
a tackifying resin selected from hydrogenated hydrocarbon resins, hydrocarbon resins and synthetic polyterpene resins;
a hydrophilic polymer selected from poly(N-vinyl lactams), poly(N-vinyl amides), poly(N-vinyl acrylamides), poly(N-alkylacrylamides), polyacrylic acids, polymethacrylic acids, polyvinyl alcohol, polyvinylamine, cellulose derivatives, polysaccharides, and copolymers and blends thereof;
a third polymer selected from low molecular weight polyalkylene glycols, low molecular weight polyalcohols, monomeric and oligomeric alkylene glycols, ether alcohols, carbonic diacids, and alkane diols; and
phyllosilicate particles comprised of a clay mineral that swells in the presence of water.

16. The composition of claim 15, wherein the hydrophobic polymer is a styrene-isoprene-styrene block copolymer.

17. The composition of claim 15, wherein the elastomeric plasticizer is a low molecular weight polyisoprene rubber.

18. The composition of claim 15, wherein the tackifying resin is a hydrogenated hydrocarbon resin.

19. The composition of claim 15, wherein the hydrophilic polymer is selected from poly(N-vinyl lactams), poly(N-vinyl amides), poly(N-alkylacrylamides), and copolymers and blends thereof.

20. The composition of claim 15, wherein the third polymer is a low molecular weight polyalkylene glycol.

21. The composition of claim 15, wherein the phyllosilicate is montmorillonite.

22. An adhesive cushion for application to the skin, comprising: a skin-contacting layer of the adhesive composition of claim 1, and a backing layer.

23. A wound dressing comprising a laminated composite of a body facing layer having a body-contacting surface, and an outwardly facing non-occlusive backing layer, wherein at least a portion of the body-contacting surface is comprised of the adhesive composition of claim 1.

24. A transdermal drug delivery device comprised of a drug reservoir containing a therapeutically effective amount of an active agent, an outwardly facing backing layer, and a means for affixing the device to a body surface comprising the adhesive composition of claim 1.

25. An oral care product for application to the teeth, comprising: a tooth contacting layer of the adhesive composition of claim 1, and a backing layer.

26. An oral care product for application to the oral mucosa, comprising: a mucosal-contacting layer of the adhesive composition of claim 1, and a backing layer.

27. The composition of claim 1, wherein the clay particles are comprised of phyllosilicate.

28. The composition of claim 27, wherein the phyllosilicate is montmorillonite.

29. The composition of claim 1, wherein the tackifying resin is a terpene resin.

30. The composition of claim 1, wherein the tackifying resin is a hydrogenated hydrocarbon resin.

31. The composition of claim 1, wherein the tackifying resin is a hydrocarbon resin.

* * * * *